US011918202B2

(12) United States Patent
Deuel et al.

(10) Patent No.: US 11,918,202 B2
(45) Date of Patent: Mar. 5, 2024

(54) SUTURE BASED CLOSURE DEVICE FOR USE WITH ENDOSCOPE

(71) Applicant: BOSTON SCIENTIFIC SCIMED, INC., Maple Grove, MN (US)

(72) Inventors: Christopher R. Deuel, Melrose, MA (US); Shaun D. Comee, Fiskdale, MA (US); Stan Gilbert, Litchfield, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 406 days.

(21) Appl. No.: 16/875,343

(22) Filed: May 15, 2020

(65) Prior Publication Data

US 2020/0360011 A1    Nov. 19, 2020

Related U.S. Application Data

(60) Provisional application No. 62/848,985, filed on May 16, 2019.

(51) Int. Cl.
*A61B 17/04*  (2006.01)
*A61B 17/00*  (2006.01)
*A61B 17/06*  (2006.01)

(52) U.S. Cl.
CPC ...... *A61B 17/0469* (2013.01); *A61B 2017/00004* (2013.01); *A61B 2017/0034* (2013.01);
(Continued)

(58) Field of Classification Search
CPC ...... A61B 17/0469; A61B 2017/00004; A61B 2017/0034; A61B 2017/047; A61B 2017/0472; A61B 2017/0609
See application file for complete search history.

(56) References Cited

U.S. PATENT DOCUMENTS 5,389,103 A * 2/1995 Melzer .............. A61B 17/0469
606/147
5,468,251 A * 11/1995 Buelna .............. A61B 17/0493
606/139
(Continued)

FOREIGN PATENT DOCUMENTS

CA         2682488 A1   10/2008
DE    202005022017 U1    5/2012
(Continued)

OTHER PUBLICATIONS

Invitation to Pay Additional Fees dated Aug. 5, 2020 for International Application No. PCT/US2020/033179.
(Continued)

*Primary Examiner* — Alexander J Orkin
(74) *Attorney, Agent, or Firm* — Seager, Tufte & Wickhem, LLP

(57) ABSTRACT

A suture device for use in combination with a delivery system including a lumen extending through the delivery system includes a needle usable to carry a suture, a distal shuttle configured to releasably secure the needle, a sleeve disposable over the distal shuttle, the distal shuttle movable relative to the sleeve between a locked position in which the needle is locked to the distal shuttle and an unlocked position in which the needle is releasable from the distal shuttle. A shaft is operably coupled to the sleeve and a control wire is operably coupled to the distal shuttle. A needle may include a needle cap.

15 Claims, 29 Drawing Sheets

(52) U.S. Cl.
CPC . *A61B 2017/047* (2013.01); *A61B 2017/0472* (2013.01); *A61B 2017/0609* (2013.01)

(56) References Cited

U.S. PATENT DOCUMENTS

| | | | |
|---|---|---|---|
| 5,478,344 | A | 12/1995 | Stone |
| 5,584,861 | A | 12/1996 | Swain et al. |
| 5,792,153 | A * | 8/1998 | Swain ............... A61B 17/0469 606/139 |
| 5,817,110 | A * | 10/1998 | Kronner ............ A61B 17/0469 606/147 |
| 5,865,836 | A * | 2/1999 | Miller ................... A61B 17/06 606/228 |
| 6,086,608 | A | 7/2000 | Ek et al. |
| 6,200,329 | B1 | 3/2001 | Fung et al. |
| 6,494,888 | B1 | 12/2002 | Laufer et al. |
| 6,506,196 | B1 | 1/2003 | Laufer |
| 6,554,845 | B1 | 4/2003 | Fleenor et al. |
| 6,569,085 | B2 | 5/2003 | Kortenbach et al. |
| 6,626,917 | B1 | 9/2003 | Craig |
| 6,663,639 | B1 | 12/2003 | Laufer et al. |
| 6,719,763 | B2 | 4/2004 | Chung et al. |
| 6,740,030 | B2 | 5/2004 | Martone et al. |
| 6,746,457 | B2 | 6/2004 | Dana et al. |
| 6,755,843 | B2 | 6/2004 | Chung et al. |
| 6,773,441 | B1 | 8/2004 | Laufer et al. |
| 6,808,491 | B2 | 10/2004 | Kortenbach et al. |
| 6,821,285 | B2 | 11/2004 | Laufer et al. |
| 6,835,200 | B2 | 12/2004 | Laufer et al. |
| 6,908,427 | B2 | 6/2005 | Fleener et al. |
| 6,997,931 | B2 | 2/2006 | Sauer et al. |
| 7,056,284 | B2 | 6/2006 | Martone et al. |
| 7,063,710 | B2 | 6/2006 | Takamoto et al. |
| 7,063,715 | B2 | 6/2006 | Onuki et al. |
| 7,094,246 | B2 | 8/2006 | Anderson et al. |
| 7,144,401 | B2 | 12/2006 | Yamamoto et al. |
| 7,147,646 | B2 | 12/2006 | Dana et al. |
| 7,153,314 | B2 | 12/2006 | Laufer et al. |
| 7,220,266 | B2 | 5/2007 | Gambale |
| 7,232,445 | B2 | 6/2007 | Kortenbach et al. |
| 7,235,086 | B2 | 6/2007 | Sauer et al. |
| 7,326,221 | B2 | 2/2008 | Sakamoto et al. |
| 7,344,545 | B2 | 3/2008 | Takemoto et al. |
| 7,347,863 | B2 | 3/2008 | Rothe et al. |
| 7,361,180 | B2 | 4/2008 | Saadat et al. |
| 7,530,985 | B2 | 5/2009 | Takemoto et al. |
| 7,601,161 | B1 | 10/2009 | Nobles et al. |
| 7,618,425 | B2 | 11/2009 | Yamamoto et al. |
| 7,713,277 | B2 | 5/2010 | Laufer et al. |
| 7,722,633 | B2 | 5/2010 | Laufer et al. |
| 7,727,246 | B2 | 6/2010 | Sixto, Jr. et al. |
| 7,736,373 | B2 | 6/2010 | Laufer et al. |
| 7,776,057 | B2 | 8/2010 | Laufer et al. |
| 7,776,066 | B2 | 8/2010 | Onuki et al. |
| 7,842,051 | B2 | 11/2010 | Dana et al. |
| 7,846,180 | B2 | 12/2010 | Cerier |
| 7,857,823 | B2 | 12/2010 | Laufer et al. |
| 7,896,893 | B2 | 3/2011 | Laufer et al. |
| 7,918,867 | B2 | 4/2011 | Dana et al. |
| 7,951,157 | B2 | 5/2011 | Gambale |
| 7,992,571 | B2 | 8/2011 | Gross et al. |
| 7,993,368 | B2 | 8/2011 | Gambale et al. |
| 8,016,840 | B2 | 9/2011 | Takemoto et al. |
| 8,021,376 | B2 | 9/2011 | Takemoto et al. |
| 8,057,494 | B2 | 11/2011 | Laufer et al. |
| 8,062,314 | B2 | 11/2011 | Sixto, Jr. et al. |
| 8,066,721 | B2 | 11/2011 | Kortenbach et al. |
| 8,105,355 | B2 | 1/2012 | Page et al. |
| 8,211,123 | B2 | 7/2012 | Gross et al. |
| 8,216,253 | B2 | 7/2012 | Saadat et al. |
| 8,226,667 | B2 | 7/2012 | Viola et al. |
| 8,277,468 | B2 | 10/2012 | Laufer et al. |
| 8,287,554 | B2 | 10/2012 | Cerier et al. |
| 8,287,556 | B2 | 10/2012 | Gilkey et al. |
| 8,308,765 | B2 | 11/2012 | Saadat et al. |
| 8,313,496 | B2 | 11/2012 | Sauer et al. |
| 8,361,089 | B2 | 1/2013 | Chu |
| 8,388,632 | B2 | 3/2013 | Gambale |
| 8,425,555 | B2 | 4/2013 | Page et al. |
| 8,454,631 | B2 | 6/2013 | Viola et al. |
| 8,480,691 | B2 | 7/2013 | Dana et al. |
| 8,540,735 | B2 | 9/2013 | Mitelberg et al. |
| 8,551,120 | B2 | 10/2013 | Gambale |
| 8,585,720 | B2 | 11/2013 | Gross et al. |
| 8,632,553 | B2 | 1/2014 | Sakamoto et al. |
| 8,679,136 | B2 | 3/2014 | Mitelberg |
| 8,709,022 | B2 | 4/2014 | Stone et al. |
| 8,764,771 | B2 | 7/2014 | Chu |
| 8,882,785 | B2 | 11/2014 | DiCesare et al. |
| 8,926,634 | B2 | 1/2015 | Rothe et al. |
| 8,992,570 | B2 | 3/2015 | Gambale et al. |
| 9,011,466 | B2 | 4/2015 | Adams et al. |
| 9,089,325 | B2 | 7/2015 | Mitelberg et al. |
| 9,125,646 | B2 | 9/2015 | Woodard, Jr. et al. |
| 9,198,562 | B2 | 12/2015 | Mitelberg et al. |
| 9,320,515 | B2 | 4/2016 | Dana et al. |
| 9,486,126 | B2 | 11/2016 | West et al. |
| 9,504,465 | B2 | 11/2016 | Chu |
| 9,510,817 | B2 | 11/2016 | Saadat et al. |
| 9,549,728 | B2 | 1/2017 | Chu |
| 9,750,494 | B2 | 9/2017 | Gross et al. |
| 9,788,831 | B2 | 10/2017 | Mitelberg |
| 9,844,366 | B2 | 12/2017 | Woodard, Jr. et al. |
| 9,867,610 | B2 | 1/2018 | Mitelberg et al. |
| 10,045,871 | B2 | 8/2018 | Saadat et al. |
| 10,143,463 | B2 | 12/2018 | Dana et al. |
| 10,194,902 | B2 | 2/2019 | Nobles et al. |
| 10,335,142 | B2 | 7/2019 | Raybin et al. |
| 10,932,771 | B2 * | 3/2021 | Comee ................... A61B 1/018 |
| 2002/0107530 | A1 | 8/2002 | Sauer et al. |
| 2003/0195529 | A1 | 10/2003 | Takamoto |
| 2003/0204205 | A1 | 10/2003 | Sauer et al. |
| 2004/0002699 | A1 | 1/2004 | Ryan et al. |
| 2004/0138706 | A1 | 7/2004 | Abrams et al. |
| 2005/0033319 | A1 | 2/2005 | Gambale et al. |
| 2005/0070959 | A1 * | 3/2005 | Cichocki .......... A61B 17/06066 606/222 |
| 2005/0250985 | A1 | 11/2005 | Saadat et al. |
| 2006/0282094 | A1 | 12/2006 | Stokes et al. |
| 2007/0118151 | A1 * | 5/2007 | Davidson ........... A61B 17/0469 606/151 |
| 2007/0270908 | A1 | 11/2007 | Stokes et al. |
| 2008/0086148 | A1 | 4/2008 | Baker et al. |
| 2009/0012538 | A1 * | 1/2009 | Saliman ............. A61B 17/0491 606/228 |
| 2009/0177031 | A1 | 7/2009 | Surti et al. |
| 2010/0137681 | A1 | 6/2010 | Ewers et al. |
| 2010/0198006 | A1 | 8/2010 | Greenburg et al. |
| 2011/0028998 | A1 * | 2/2011 | Adams ............... A61B 17/0482 606/145 |
| 2011/0160731 | A1 | 6/2011 | Bleich et al. |
| 2011/0276064 | A1 * | 11/2011 | Henrichsen ........ A61B 17/0469 606/145 |
| 2012/0158023 | A1 | 6/2012 | Miltelberg et al. |
| 2012/0271327 | A1 | 10/2012 | West et al. |
| 2012/0277768 | A1 | 11/2012 | Viola |
| 2013/0096581 | A1 | 4/2013 | Gilkey et al. |
| 2013/0304093 | A1 | 11/2013 | Serina et al. |
| 2014/0121457 | A1 | 5/2014 | Mort et al. |
| 2014/0128668 | A1 | 5/2014 | Cox et al. |
| 2015/0126983 | A1 | 5/2015 | Alvarado et al. |
| 2016/0045197 | A1 | 2/2016 | Mitelberg et al. |
| 2017/0042534 | A1 | 2/2017 | Nobles et al. |
| 2017/0086817 | A1 | 3/2017 | Mitelberg |
| 2017/0086818 | A1 | 3/2017 | Mitelberg |
| 2017/0086819 | A1 * | 3/2017 | Raybin ............ A61B 17/06066 |
| 2017/0119371 | A1 | 5/2017 | Mims et al. |
| 2017/0319197 | A1 | 11/2017 | Gross et al. |
| 2018/0042602 | A1 | 2/2018 | Mitelberg et al. |
| 2018/0042603 | A1 | 2/2018 | Mitelberg et al. |
| 2018/0153381 | A1 | 6/2018 | Wei et al. |
| 2018/0221009 | A1 | 8/2018 | Mitelberg et al. |

(56) References Cited

U.S. PATENT DOCUMENTS

| | | |
|---|---|---|
| 2018/0235604 A1 | 8/2018 | Comee et al. |
| 2018/0344501 A1 | 12/2018 | Saadat et al. |
| 2019/0380702 A1 | 12/2019 | Deuel et al. |

FOREIGN PATENT DOCUMENTS

| | | |
|---|---|---|
| EP | 1354558 A2 | 10/2003 |
| EP | 1520509 A1 | 4/2005 |
| EP | 2108304 A2 | 10/2009 |
| JP | H07250840 A | 10/1995 |
| WO | 0101868 A1 | 1/2001 |
| WO | 0189393 A1 | 11/2001 |
| WO | 2008016592 A2 | 2/2008 |
| WO | 2008045376 A2 | 4/2008 |
| WO | 2008098124 A1 | 8/2008 |
| WO | 2010036227 A1 | 4/2010 |
| WO | 2010085793 A2 | 7/2010 |
| WO | 2016200811 A1 | 12/2016 |
| WO | 2017087856 A1 | 5/2017 |
| WO | 2018156603 A1 | 8/2018 |
| WO | 2020006122 A1 | 1/2020 |

OTHER PUBLICATIONS

International Search Report and Written Opinion dated Aug. 20, 2019 for International Application No. PCT/US2019/033748.
International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
International Search Report and Written Opinion dated Nov. 18, 2019 for International Application No. PCT/US2019/049774.
International Search Report and Written Opinion dated Sep. 20, 2019 for International Application No. PCT/US2019/039312.
International Search Report and Written Opinion dated May 22, 2018 for International Application No. PCT/US2018/018982 (12 pgs).
International Preliminary Report on Patentabiliy dated Sep. 6, 2019 for International Application No. PCTUS2018018982.

* cited by examiner

SUTURE BASED CLOSURE DEVICE FOR USE WITH ENDOSCOPE

CROSS-REFERENCE TO RELATED APPLICATIONS

This application claims the benefit of priority under 35 U.S.C. § 119 to U.S. Provisional Application Ser. No. 62/848,985 filed May 16, 2019, the entirety of which is incorporated herein by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for known closure methods. Examples of such endoscopic treatments include removal of large lesions, tunneling under the mucosal layer, full thickness removal of tissue, treating other organs by passing outside of the gastrointestinal tract, and post-surgical repairs such as post-surgical leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. An example is a suture device for use in combination with an endoscope. The suture device includes a needle that is configured to carry a suture, the needle having a distal end. A needle cap is configured to releasably fit over the distal end of the needle.

Another example is a suture device for use in combination with an endoscope having a working channel and a distal end. The suture device includes a needle that is configured to carry a suture, the needle including a distal end and a distal detent near the distal end. A needle cap is configured to releasably fit over the distal end of the needle. A distal shuttle is configured to releasably secure the needle. A sleeve is disposable over the distal shuttle and is movable between a locked position in which the needle is secured to the distal shuttle and an unlocked position in which the needle is releasable from the distal shuttle.

Alternatively or additionally, the needle cap may be formed of a biocompatible polymer.

Alternatively or additionally, the needle cap may be formed of a biosorbable polymer.

Alternatively or additionally, the needle cap may include a cylindrical needle cap body defining a void that is configured to fit over the needle and an atraumatic distal tip.

Alternatively or additionally, the needle cap may further include one or more elongate slots extending axially within the cylindrical needle cap body.

Alternatively or additionally, the needle cap may further include one or more convex protuberances extending in to the void, the one or more convex protuberances configured to fit into the distal detent of the needle.

Alternatively or additionally, the needle cap may be configured to be pushed off of the needle by moving the sleeve distally.

Another example is a suture device for use in combination with an endoscope having a working channel and a distal end. The suture device includes a translation assembly that is configured to be axially translatable within the working channel and that includes a needle configured to carry a suture, a distal shuttle that is configured to releasably secure the needle and a sleeve that is disposable over the distal shuttle. The sleeve is movable between a locked position in which the needle is secured to the distal shuttle and an unlocked position in which the needle is releasable from the distal shuttle, the sleeve including an elongate groove extending axially along the sleeve, the elongate groove configured to accommodate the suture extending therethrough. The suture device includes a distal endcap that is securable to the distal end of the endoscope and is configured to engage the needle when the needle is advanced distally into the distal endcap and to release the needle when the needle is locked to the distal shuttle and the distal shuttle is withdrawn proximally.

Alternatively or additionally, the distal shuttle may include a distal needle opening that is configured to accommodate the needle when the distal shuttle is advanced distally over the needle, one or more bearing ball openings arranged orthogonal to the distal needle opening such that the one or more bearing ball openings align with a proximal detent of the needle when the needle is secured to the distal shuttle, and one or more bearing balls that are disposed within the one or more bearing ball openings and disposable within the proximal detent when the needle is secured to the distal shuttle.

Alternatively or additionally, the sleeve may include one or more sleeve openings that are smaller in diameter than the one or more bearing balls. When in the locked position, the one or more sleeve openings are misaligned with the one or more bearing ball openings such that the one or more bearing balls engage the proximal detent of the needle, and when in the unlocked position, the one or more sleeve openings are aligned with the one or more bearing ball openings such that the one or more bearing balls can move radially outward a distance sufficient to permit the one or more bearing balls to clear the proximal detent of the needle.

Another example is a suture device for use in combination with a delivery system including a lumen extending through the delivery system. The suture device includes a suture translation assembly that is configured to be axially translatable within the lumen of the delivery system and that includes a needle usable to carry a suture and a distal shuttle configured to releasably secure the needle. A sleeve is disposable over the distal shuttle and is movable relative to the sleeve between a locked position in which the needle is locked to the distal shuttle and an unlocked position in which the needle is releasable from the distal shuttle. A suture catheter is operably coupled to the sleeve and a control wire is operably coupled to the distal shuttle. A distal endcap is configured to be securable to the distal end of the delivery system and to releasably engage and disengage the needle, the endcap configured to engage the needle when the needle is advanced distally into the endcap, and to release the needle when the needle is locked to the distal shuttle and the distal shuttle is withdrawn proximally.

Alternatively or additionally, moving the control wire proximally may cause the distal shuttle to move proximally relative to the sleeve, thereby locking the needle to the distal shuttle.

Alternatively or additionally, moving the control wire distally may cause the distal shuttle to move distally relative to the sleeve, thereby releasing the needle from the distal shuttle.

Alternatively or additionally, the needle may include a distal region and a proximal region, the distal region including a distal detent for releasably engaging the distal endcap and the proximal region including a proximal detent for releasably engaging the distal shuttle.

Alternatively or additionally, the distal shuttle may include one or more bearing ball openings that are arranged to align with the proximal detent when the needle is secured to the distal shuttle and one or more bearing balls that are disposed within the one or more bearing ball openings and are disposable within the proximal detent when the needle is secured to the distal shuttle.

Alternatively or additionally, the sleeve may include one or more sleeve openings smaller in diameter than the one or more bearing balls. When in the locked position, the one or more sleeve openings are misaligned with the one or more bearing ball openings such that the one or more bearing balls engage the proximal detent of the needle and when in the unlocked position, the one or more sleeve openings are aligned with the one or more bearing ball openings such that the one or more bearing balls can move radially outward a distance sufficient to permit the one or more bearing balls to clear the proximal detent of the needle.

Alternatively or additionally, the suture device may further include a yoke that is operably coupled to the control wire, the yoke coupling the control wire to the distal shuttle via a pin that extends through the yoke and translates along a pair of slots formed in the sleeve.

Alternatively or additionally, the suture catheter may include a coil, and the coil is operably coupled to the sleeve.

Alternatively or additionally, the sleeve may be welded to the coil.

Alternatively or additionally, the control wire may extend through the suture catheter.

Alternatively or additionally, the suture device may further include a user interface that is operably coupled to the suture catheter and the control wire, the user interface configured to permit a user to move the control wire, and thus the distal shuttle, relative to the suture catheter.

Another example is a suture device for use in combination with a delivery system including a lumen extending through the delivery system. The suture device includes a needle usable to carry a suture and a distal shuttle that is configured to releasably secure the needle. A sleeve is disposable over the distal shuttle and the distal shuttle is movable relative to the sleeve between a locked position in which the needle is locked to the distal shuttle and an unlocked position in which the needle is releasable from the distal shuttle. A shaft is operably coupled to the sleeve and a control wire extends through the shaft and is operably coupled to the distal shuttle. A distal endcap is configured to be securable to a distal end of the delivery system and to releasably engage and disengage the needle, the endcap configured to engage the needle when the needle is advanced distally into the endcap, and to release the needle when the needle is locked to the distal shuttle and the distal shuttle is withdrawn proximally.

Alternatively or additionally, the suture device may further include a user interface that is configured to allow a user to manipulate the control wire relative to the shaft in order to move the distal shuttle between its locked position and its unlocked position.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
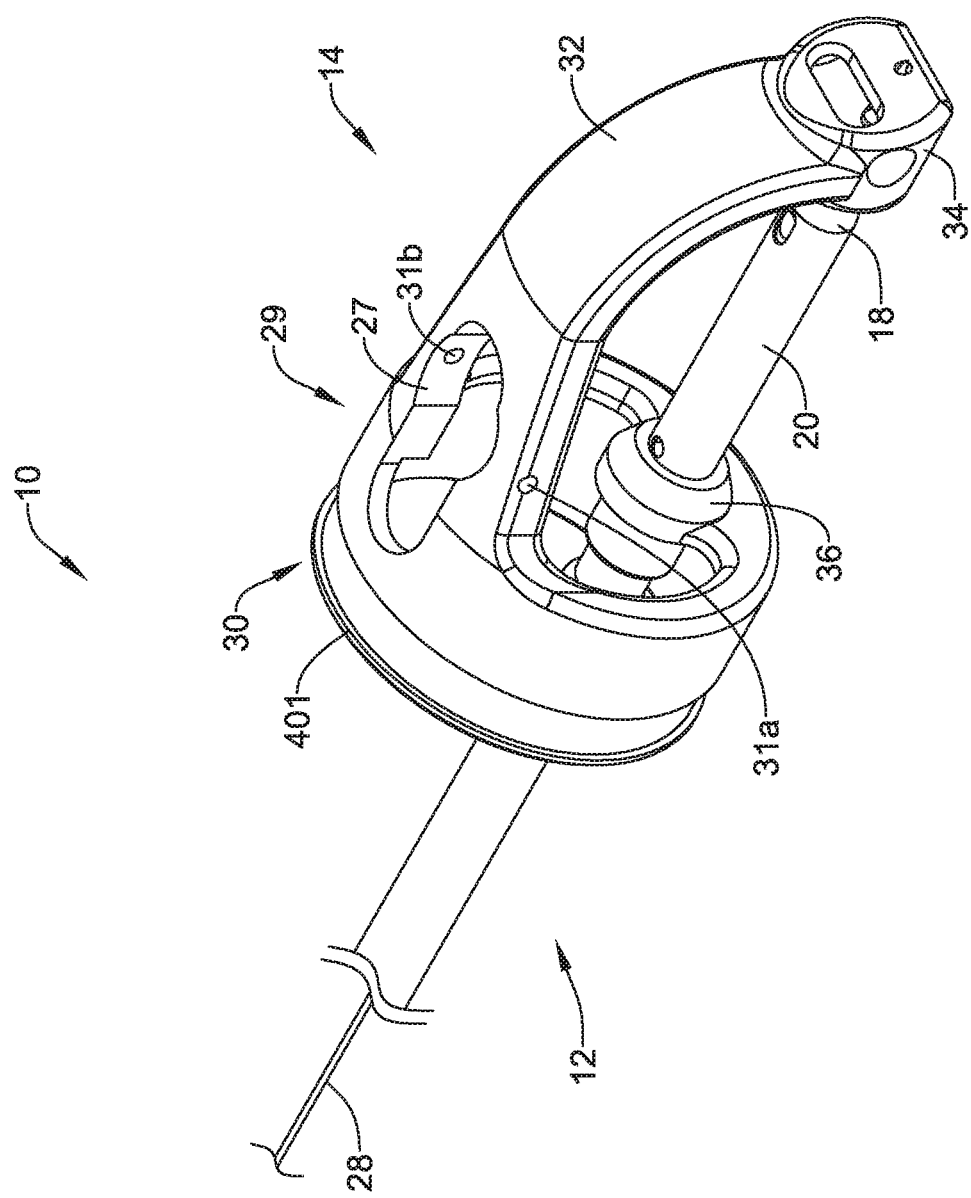
FIG. 1 is a perspective view of an illustrative suture device in accordance with an example of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used within a single working or available channel of an endoscope, and in some embodiments may be operated by a single individual, although in some embodiments a second individual may be involved. In some embodiments, the suture devices described herein may be considered as operating along a single line of operation. The device itself may be translatable distally and proximally within a working channel, and a handle portion may itself be translatable distally and proximally along the same line of operation in locking and unlocking a needle to be able to pass the needle back and forth between an active portion of the suture device and a passive portion of the suture device. The device may be configured to enable the needle to be selectively locked into either of a more distal position or a more proximal position, and the device may itself be translated distally or proximally with the needle locked in place in order to move the needle, and hence a suture, relative to the tissue being repaired.

FIG. 1 is a perspective view of a suture device 10 that may be considered as being configured for use in combination with a delivery system including a lumen that extends through the delivery system. For example, the delivery system may be an endoscope having a working channel. The delivery system may also be a catheter. It will be appreciated that there is a change in scale on either side of the break line shown. In some embodiments, the suture device 10 may be considered as including a suture translation assembly 12 that is configured to be axially translatable within the lumen of the delivery system and a distal assembly 14 that is configured to be secured to a distal end of the delivery system. The suture translation assembly 12 extends into the distal assembly 14 and includes a needle 16 that may be used to carry a suture as well as a distal shuttle 18 that is configured to releasably secure the needle 16.

A member 20 may be disposed over the distal shuttle 18 and, as will be shown in subsequent Figures, is movable between a locked position in which the needle 16 is secured to the distal shuttle 18 and an unlocked position in which the needle 16 is releasable from the distal shuttle 18. In some embodiments, for example, the member 20 may be a sleeve 20. A user interface may extend proximally from the distal shuttle 18 and the sleeve 20, and may be configured to move the sleeve 20 between the locked position and the unlocked position. A shaft 28 may extend distally to the suture translation assembly 12, and may in particular be coupled to the sleeve 20. The user interface may take a number of different forms. For examples, the user interface may be the user interface 22 as described and illustrated in U.S. Patent Application Publication No. 2018/0235604, which publication is incorporated by reference herein in its entirety. In some embodiments, the user interface may be as described in a provisional application Ser. No. 62/794,075 filed Jan. 18, 2019 and entitled ENDOSCOPIC SUTURING CONTROL HANDLE, which application is incorporated by reference herein in its entirety. In some instances, the user interface may be as described in a provisional application filed on the even date herewith, Attorney Docket No. 2001.2051100 entitled CONTROL HANDLE FOR ENDOSCOPIC SUTURING, which application is incorporated by reference herein in its entirety. These are just examples.

In some embodiments, the distal assembly 14 includes a body 29 having a proximal connector 30 that may be configured to be coupled to the distal end of an endoscope or other delivery system. In some embodiments, as illustrated, the proximal connector 30 may include a fixation feature 401. As will be discussed with respect to subsequent Figures, the fixation feature 401, which may in some embodiments be considered as being a fixation flange 401, helps to secure the distal assembly 14 to the distal end of an endoscope or other delivery system using a split ring attachment mechanism.

The body 29 includes an arm 32 that extends to an endcap 34. As will be discussed, the endcap 34 may be configured to releasably engage and disengage the needle 16. In some embodiments, for example, the endcap 34 may be configured to engage the needle 16 when the needle 16 is advanced distally into the endcap 34, and to release the needle 16 when the needle 16 is locked into the distal shuttle 18 (as will be discussed) and the distal shuttle 18 is withdrawn proximally. The distal assembly 14 may be considered as including a guide member 36 that may be secured to or integrally formed with the body 29, and may permit the suture translation assembly 12 to extend through the guide member 36 and to translate relative to the guide member 36. In some embodiments, the body 29 may include an aperture 27 that may enable other devices to be inserted through the aperture 27. In some instances, as will be discussed with respect to subsequent Figures, the aperture 27 may be configured to accommodate a side-saddled lumen attachment element. In some embodiments, the aperture 27 may include one or more of a pin aperture 31a and a pin aperture 31b that may, for example, be used to mount the aforementioned side-saddled lumen attachment element, or possibly other features as well.

Figure 2:
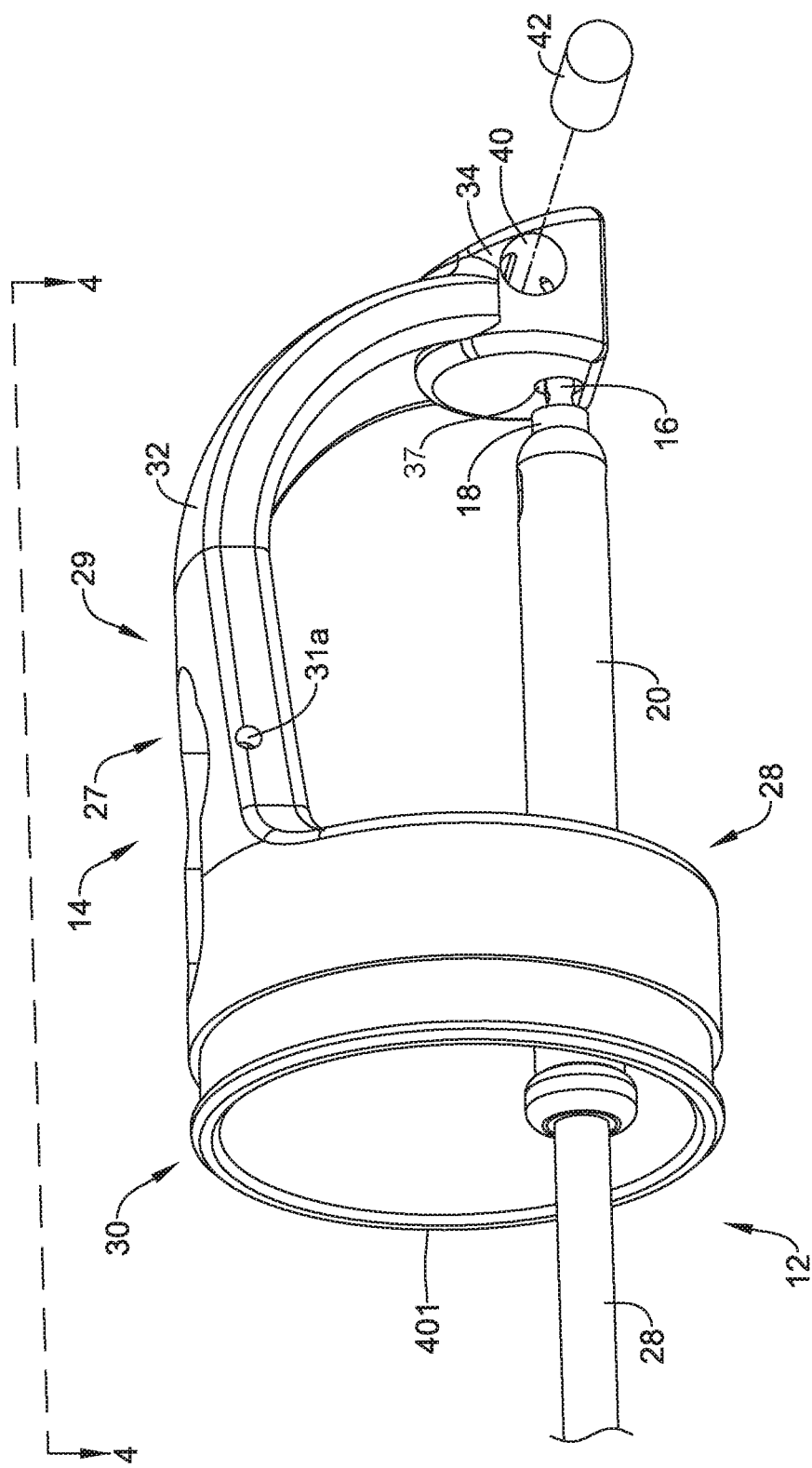
FIG. 2 is a perspective view of a distal assembly forming part of the illustrative suture device of FIG. 1, shown in an extended position.
Figure 3:
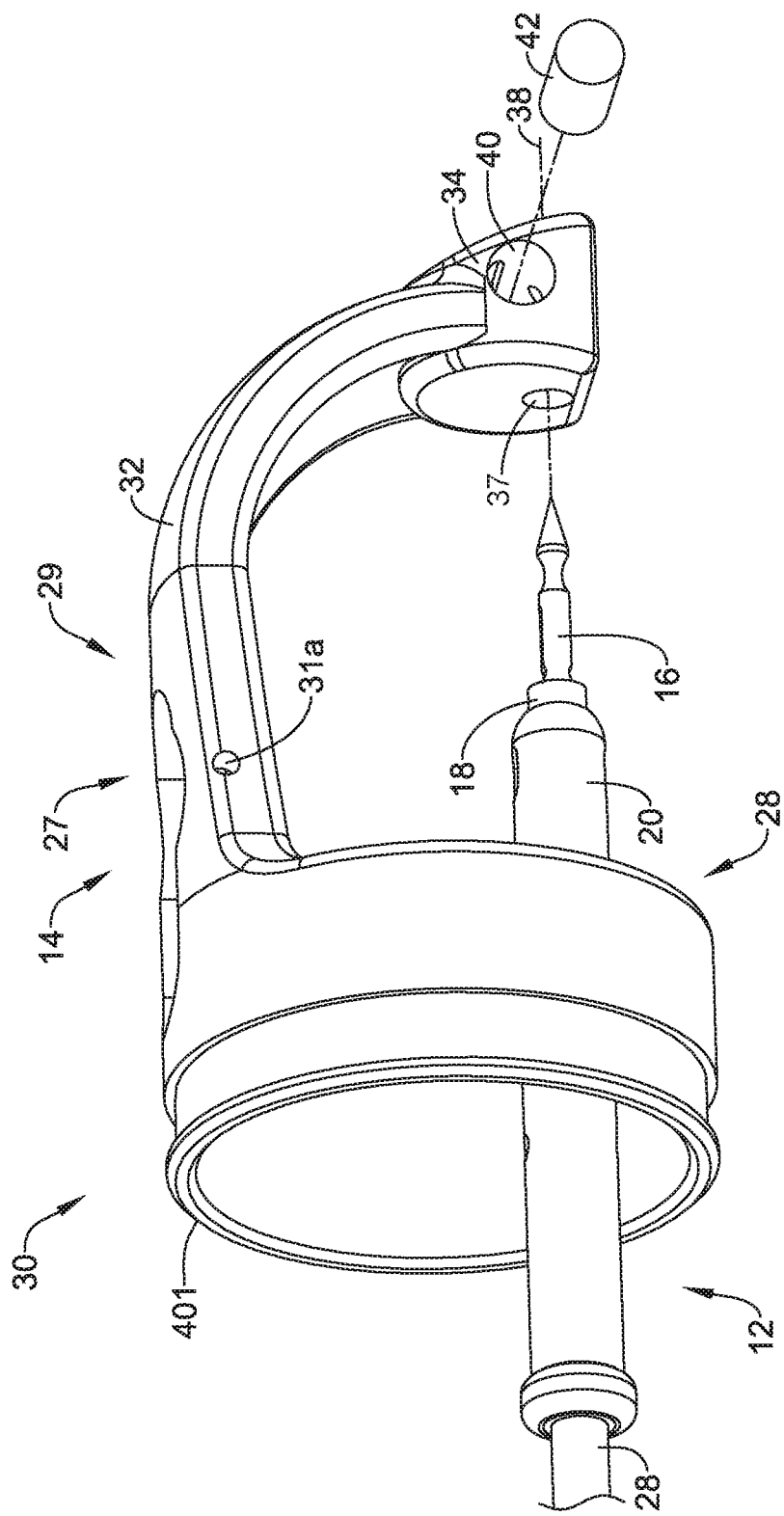
FIG. 3 is a perspective view of the distal assembly of FIG. 2, shown in a retracted position.

FIG. 2 and FIG. 3 show the suture translation assembly 12 extended through the guide member 36 and into the distal assembly 14. In FIG. 2, the suture translation assembly 12 is shown in an extended position in which the needle 16 extends into the endcap 34 while in FIG. 3, the suture translation assembly 12 is shown in a retracted position in which the needle 16 has been withdrawn proximally from the endcap 34. In some embodiments, as can be seen, the endcap 34 includes a proximal needle opening 37 that is configured to help guide the needle 16 into the proximal needle opening 37 as well as to accommodate the needle 16 when the needle 16 is advanced distally into the endcap 34. In some embodiments, the proximal needle opening 37 may extend all the way through the endcap 34 while in other cases the proximal needle opening 37 may not pass all the way through the endcap 34. In some instances, as shown, the proximal needle opening 37 may be considered as being aligned with a longitudinal axis 38 of the needle 16 (as shown in FIG. 3).

One or more securement openings 40 may be arranged orthogonal to the proximal needle opening 37 and one or more securements 42 that are configured to be disposed within the one or more securement openings 40, and which are configured to releasably engage the distal detent (as will be discussed) of the needle 16. In some embodiments, there may be a pair of securement openings 40, one on either side of the endcap 34. In some embodiments, there may be a pair of securements 42, with one disposed within each of the pair of securement openings 40. In some embodiments, while shown schematically, the one or more securements 42 may be springs or coils, for example.

Figure 4:
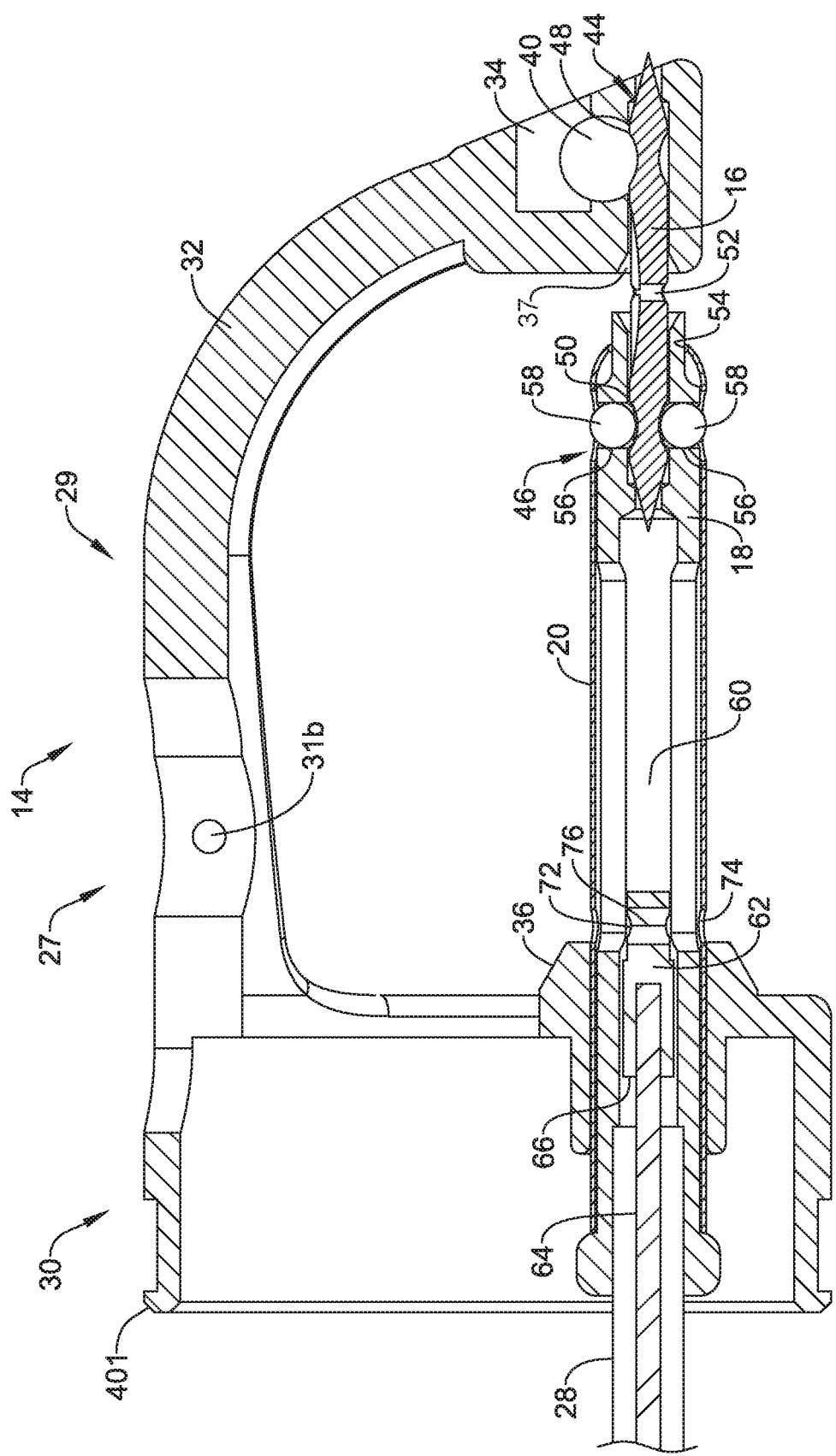
FIG. 4 is a cross-sectional view of the distal assembly of FIG. 2, taken along the line 4-4.
Figure 5:
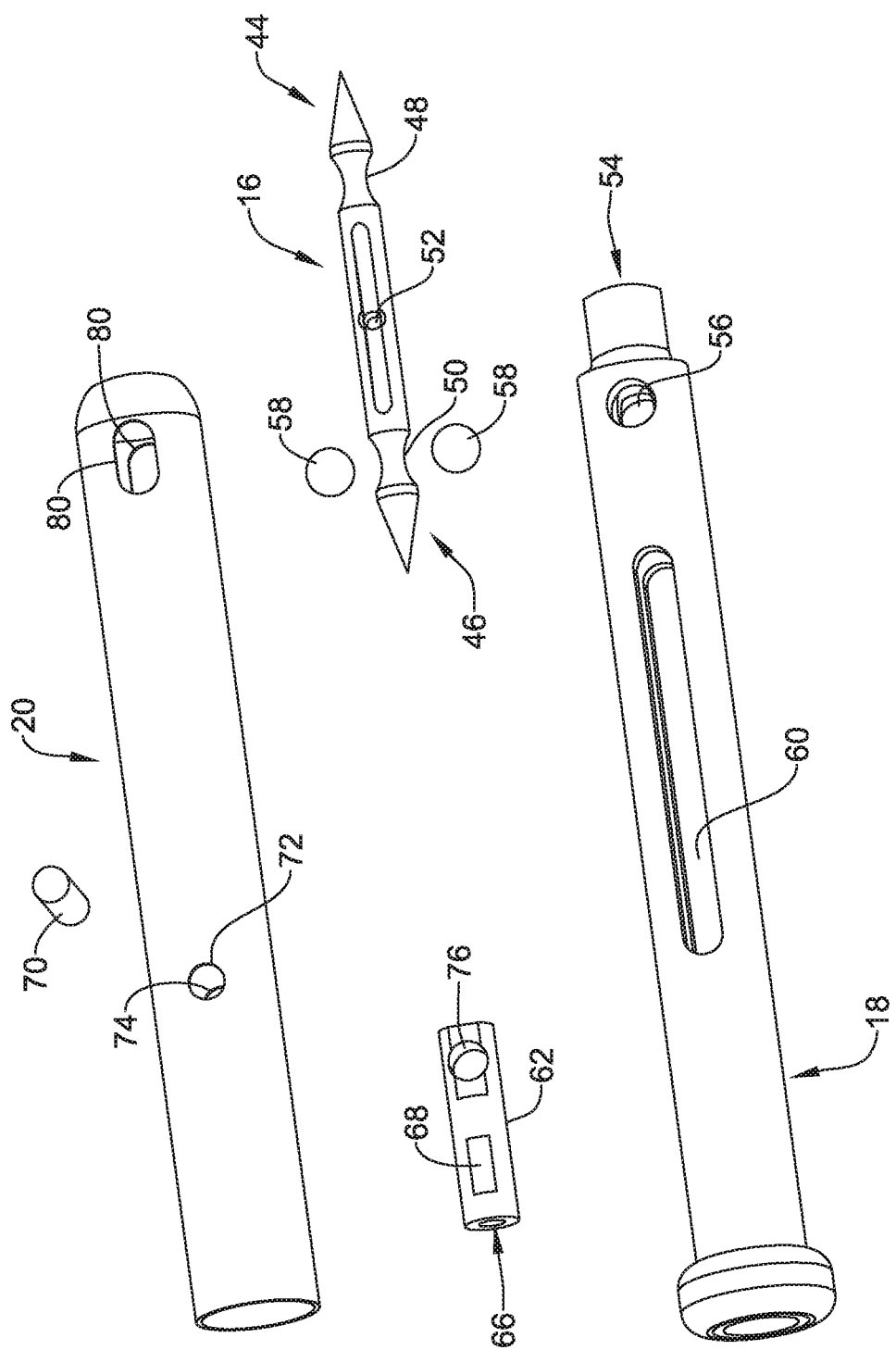
FIG. 5 is an exploded view of a portion of a suture translation assembly forming part of the illustrative suture device of FIG. 1.

FIG. 4 is a cross-sectional view of the distal assembly 14, with the suture translation assembly 12 disposed within the distal assembly 14. FIG. 5 is an exploded view of the suture translation assembly 12. The needle 16 may be considered as including a distal region 44 and a proximal region 46. In some embodiments, the distal region 44 may include a distal detent 48 for releasably engaging the endcap 34 and the proximal region 46 may include a proximal detent 50 for releasably engaging the distal shuttle 18. The needle 16 may, as shown, include an aperture 52 for accommodating a suture line passing therethrough.

In some embodiments, the distal shuttle 18 may be considered as including a distal needle opening 54 that is configured to accommodate the needle 16 when the distal shuttle 18 is advanced distally over the needle 16 and that is aligned with the longitudinal axis 38 of the needle 16. One or more bearing ball openings 56 may be arranged orthogonal to the distal needle opening 54 such that the one or more bearing ball openings 56 align with the proximal detent 50 when the needle 16 is secured to the distal shuttle 18. In some embodiments, one or more bearing balls 58 may be disposed within the one or more bearing ball openings 56 and may be configured to be disposed within the proximal detent 50 when the needle is secured to the distal shuttle 18.

In some embodiments, the distal shuttle 18 includes an internal void 60 and a sleeve capture member 62 that is slidingly disposed within the internal void 60. In some embodiments, the sleeve capture member 62 may be coupled to a cable 64 extending distally within the shaft 28 and into a cable aperture 66 and secured via a crimp or other mechanical connection 68. In some embodiments, the sleeve capture member 62 may be coupled to the sleeve 20 via a pin 70 that extends through first and second sleeve connection apertures 72, 74 and a corresponding aperture 76 extending through the sleeve capture member 62 as well as extending through the internal void 60.

Figure 6:
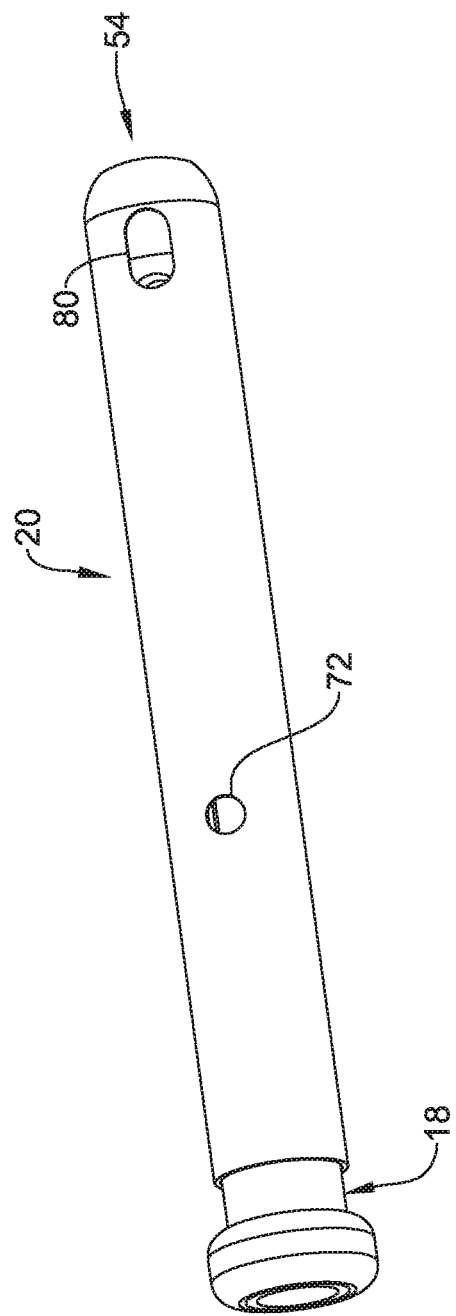
FIG. 6 is a side view of a distal shuttle and a member forming part of the suture translation assembly, with the member shown extended in a locked position.

In some embodiments, the sleeve 20 includes one or more sleeve openings 80 that may be smaller in diameter, or smaller in width, than the diameter of the one or more bearing balls 58. In some embodiments, the sleeve 20 may include a pair of sleeve openings 80, corresponding to a pair of bearing ball openings 56 and a pair of bearing balls 58. When the sleeve 20 is in the locked position, as shown for example in FIG. 6, the one or more sleeve openings 80 are misaligned with, or do not align with, the one or more bearing ball openings 56, and so the one or more bearing balls 58 engage the proximal detent 50 of the needle 16. The sleeve 20 prevents the one or more bearing balls 58 from being pushed out of the proximal detent 50.

Figure 7:
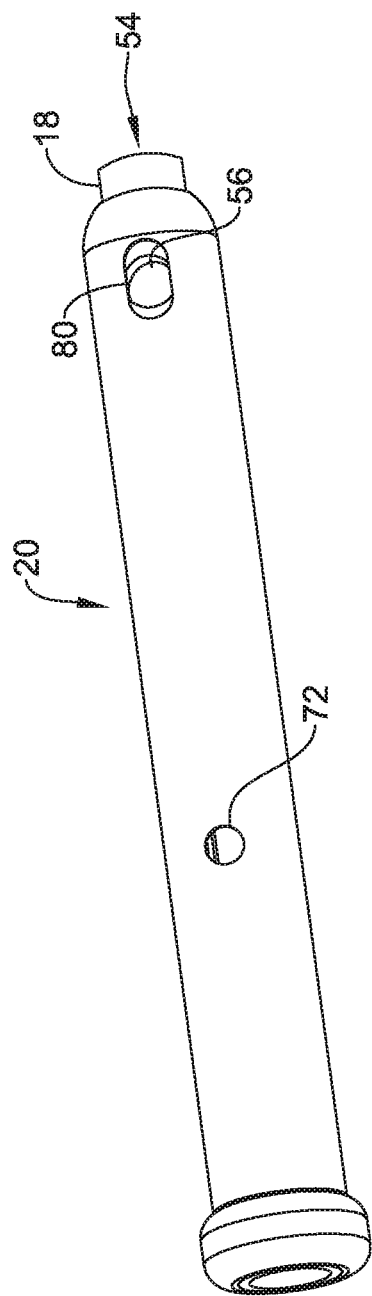
FIG. 7 is a side view of the distal shuttle and the member of FIG. 6, with the member shown retracted in an unlocked position.

Conversely, when the sleeve 20 is in the unlocked position, as shown for example in FIG. 7, the one or more sleeve openings 80 are aligned with the one or more bearing ball openings 56. This permits the one or more bearing balls 58 to move radially out, into the one or more sleeve openings 80, a distance sufficient to permit the one or more bearing balls 58 to clear the proximal detent 50 of the needle 16 in response to a force applied to the one or more bearing balls 58 by the needle 16. With reference to FIG. 4, while the suture translation assembly 12 is shown advanced into the distal assembly 14, the sleeve 20 is in the unlocked position relative to the distal shuttle 18, and thus the one or more bearing balls 58 may be seen as extending partially into the one or more sleeve openings 80.

In some cases, the suture device 10 will have a proximal handle (not shown) that allows the user to create relative movement between the sleeve 20 and the distal shuttle 18. The proximal handle may provide an indication to the user of the relative position of the sleeve 20 and the distal shuttle 18. In some cases, the proximal handle may include a soft detent or other feature that informs the user when the needle 16 is locked relative to the distal shuttle 18 and when the needle 16 is not locked relative to the distal shuttle 18.

In some cases, the sleeve 20 and the distal shuttle 18 may be modified to provide a more robust indication of when the needle 16 is locked to the distal shuttle 18 and when the needle 16 is not locked to the distal shuttle 18. In particular reference to FIG. 5, in some cases the sleeve openings 80 may be moved a short distance proximally relative to the position shown in FIG. 5. In some cases, the internal void 60, which is formed within the distal shuttle 18, may be shortened. In combination, these two changes can provide a more robust indication of when the needle 16 is locked to the distal shuttle 18 and when the needle 16 is not locked to the distal shuttle 18. Moving the sleeve 20 fully in one direction means that the needle 16 is locked to the distal shuttle 18. Moving the sleeve 20 fully in the opposite direction means that the needle 16 is not locked to the distal shuttle 18. This can provide a simple, binary locked/unlocked indication to the user.

In some embodiments, it will be appreciated that the distal shuttle 18, and the sleeve 20, in combination, provide an active connection to the needle 16 while the distal endcap 34 provides a passive connection to the needle 16. If the needle 16 is moved distally into the distal endcap 34, the distal endcap 34 will grab onto the needle 16, with the one or more securements 42 engaging the distal detent 48. If the needle 16 is subsequently moved proximally, the axial force applied overcomes any resistance provided by the one or more securements 42, and the needle 16 is able to move proximally. In contrast, the active connection to the needle 16 provided by the distal shuttle 18 and the sleeve 20, however, requires action to move the sleeve 20, relative to the distal shuttle 18, between the locked position and the unlocked position. The user interface provides a mechanism for positively moving the sleeve 20 between the locked and unlocked positions.

Figure 8:
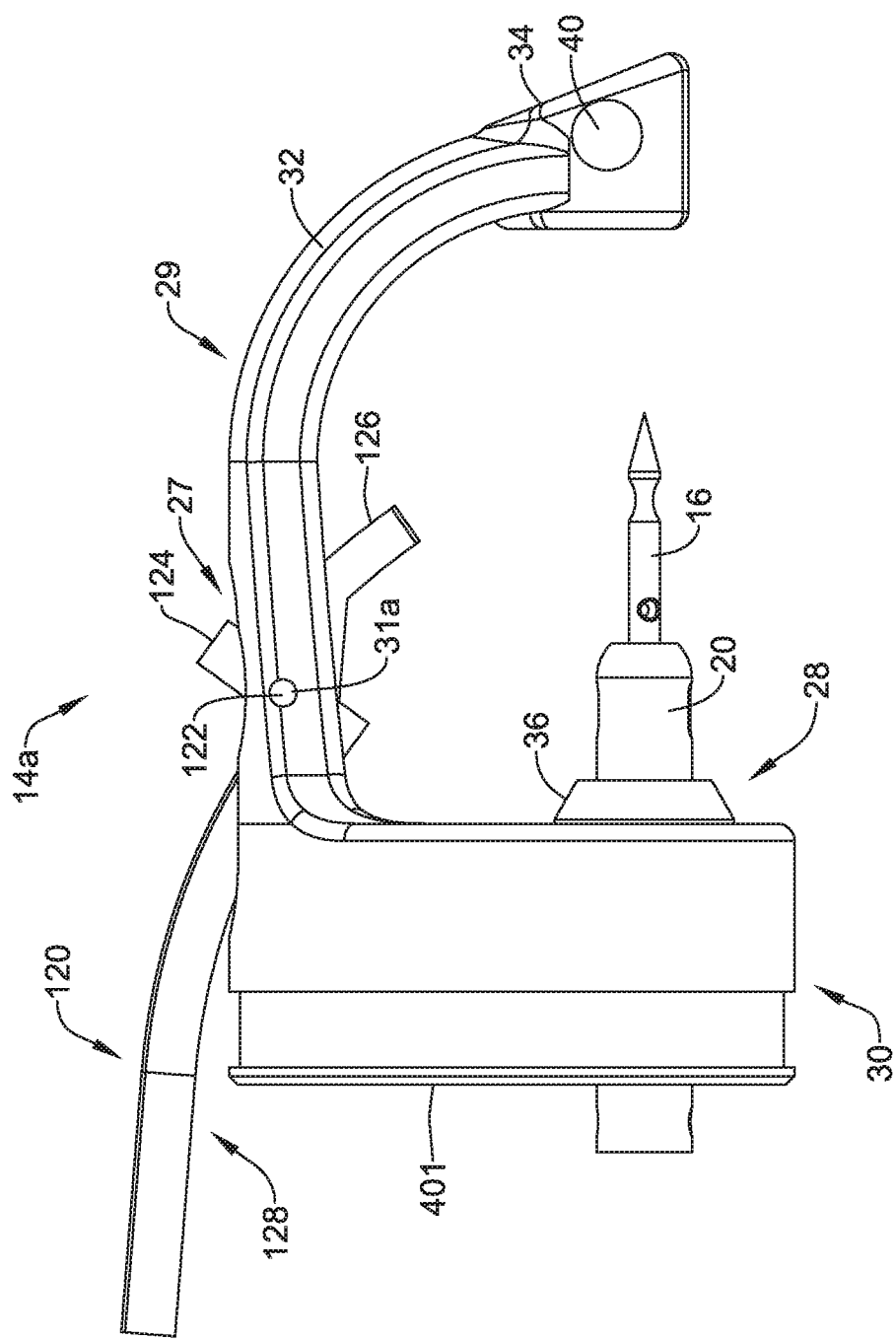
FIG. 8 is a side view of a distal assembly usable in the suture device of FIG. 1 in accordance with an example of the disclosure.

FIG. 8 is a side view of a distal assembly 14a that may, for example, be usable in the suture device 10 shown in FIG. 1. The distal assembly 14a is similar to the distal assembly 14 shown in previous Figures, but includes a side-saddled lumen attachment element 120 that is coupled to the body 29 of the distal assembly 14a. In some embodiments, the side-saddled lumen attachment element 120 may include one or two pegs 122 that fit into the pin apertures 31a and 31b (pin aperture 31a is visible in this view) and thus enable the side-saddled lumen attachment element 120 to pivot relative to the body 29 of the distal assembly 14a. In some embodiments, the side-saddled lumen attachment element 120 includes a ring 124, from which the pegs 122 extend, a distal region 126 and a body 128 that in some instances has a curvature to it.

Figure 9:
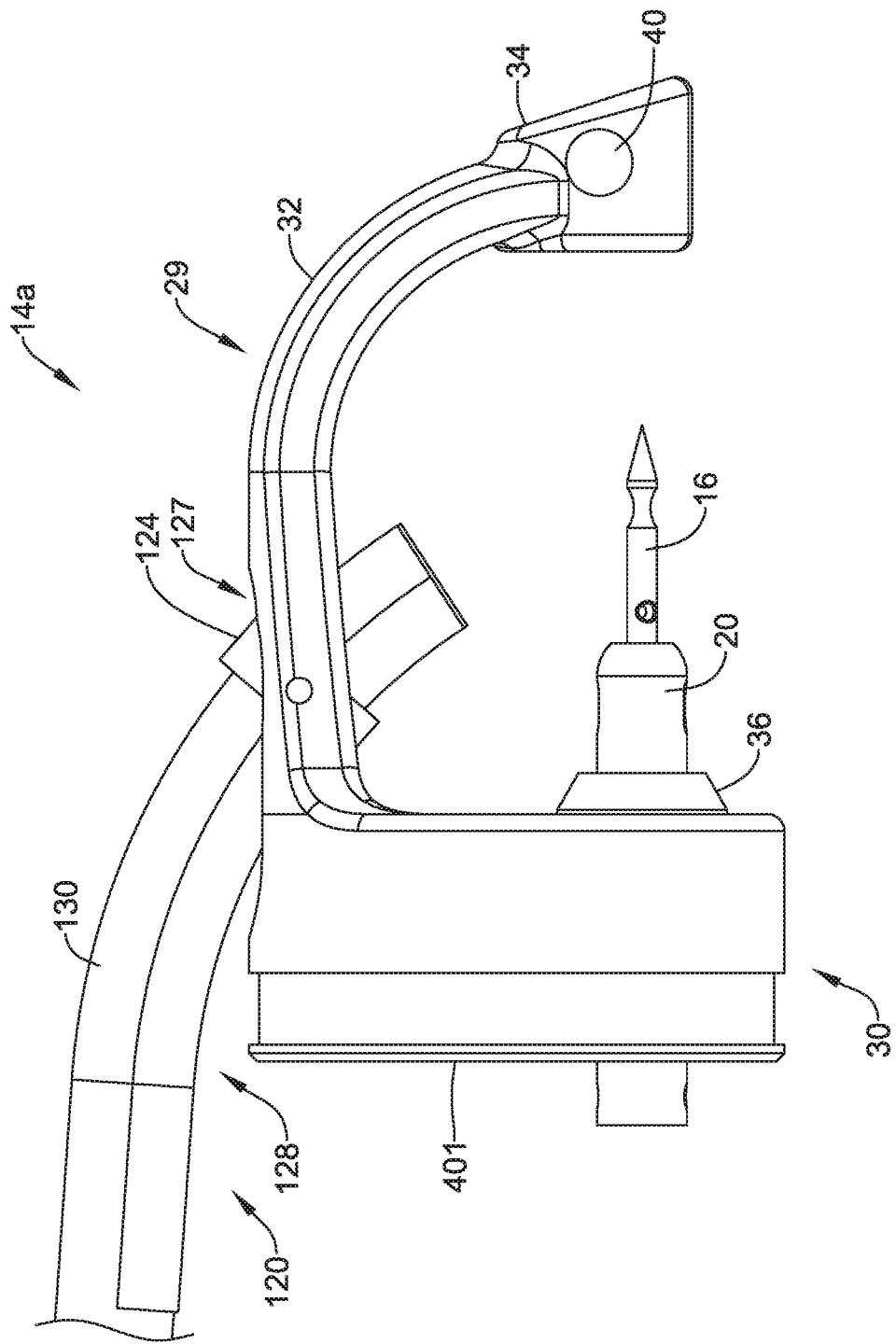
FIG. 9 is a side view of the distal assembly of FIG. 8 in combination with an attached flexible lumen.

In some embodiments, the distal region 126 and the body 128 have a semi-circular profile in order to accommodate a lumen such as a flexible lumen 130 that may engage within the side-saddled lumen attachment element 120 via a frictional or compressive fit as shown in FIG. 9. The flexible lumen 130 may be polymeric or metallic. A polymeric lumen may, for example, be expanded to a full working dimension by extending a mandrel through the flexible lumen 130 after the flexible lumen 130 has been placed relative to the side-saddled lumen attachment element 120.

In some embodiments, the side-saddled attachment element 120 (and accompanying flexible lumen 130) may be used as a secondary working channel and may contain the suture used in the procedure. In some embodiments, it may be large enough to accommodate secondary tools for use during the procedure for tissue acquisition or manipulation allowing secondary tool use without requiring a dedicated dual-channel delivery system such as a dual channel endoscope. If desired, a dual-channel delivery system could be used to provide even more options in a procedure. The side-saddled attachment element 120 may have an exit port in the distal assembly 14a such that secondary tools extend along an axis suitable for tissue manipulation. This axis may cross the axis of the suture carrying element, allowing a secondary tool to pull tissue into the suture carrying element's projected path. For example, this could be used to pull tissue in line with a needle to assist in driving the needle 16 through the tissue. Maintaining tension on the suture through the side-saddled attachment element 120 may keep the suture from interfering with the procedure.

Figure 10:
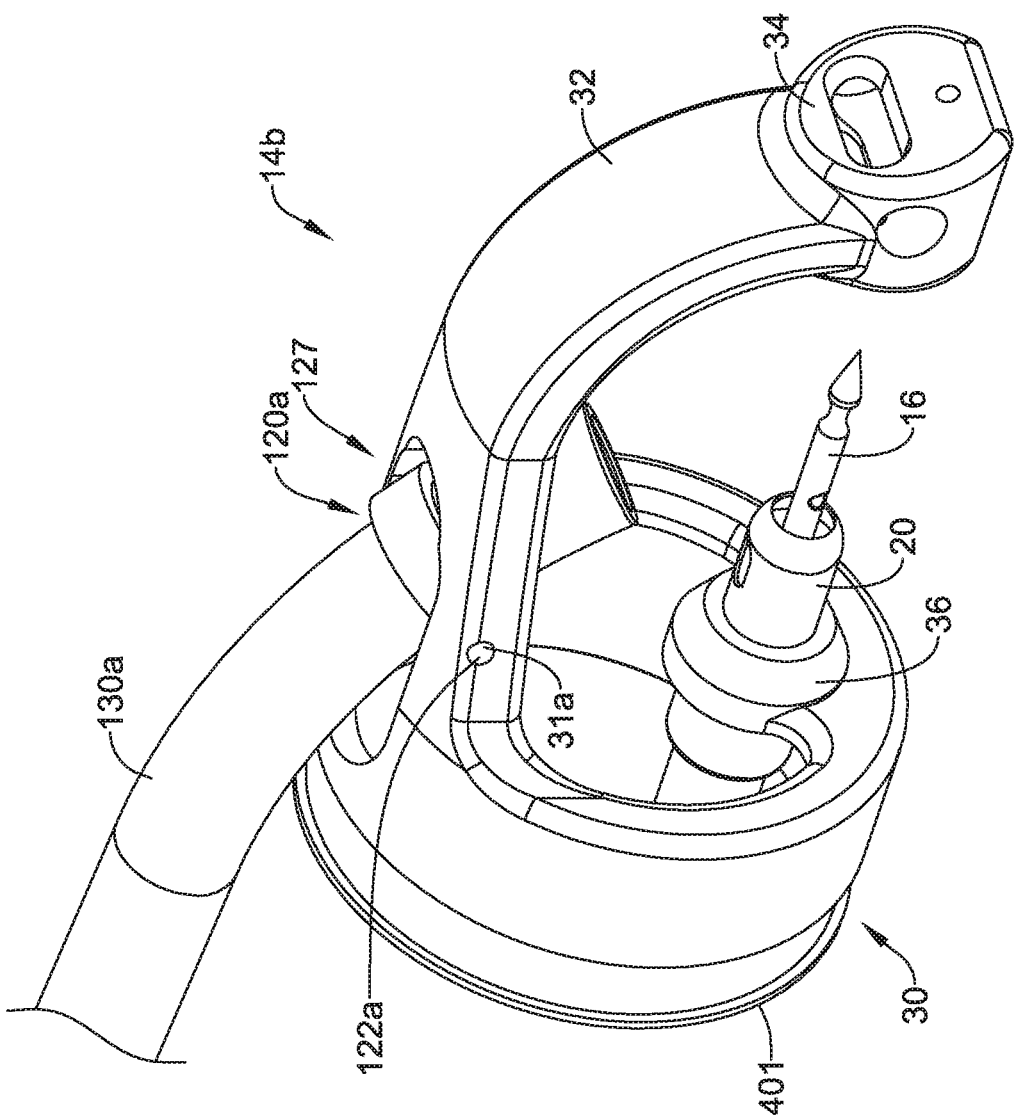
FIG. 10 is a side view of a distal assembly usable in the suture device of FIG. 1, shown with an attached lumen, in accordance with an example of the disclosure.

FIG. 10 is a perspective view of a distal assembly 14b that includes a shorter side-saddled lumen attachment element 120a that may be pivotally secured to the body 29 via one or more pegs 122a that extend into the pin apertures 31a, 31b. A lumen 130a coupled with the side-saddled lumen attachment element 120a to provide a working channel through which the suture or other tools may be extended.

Figure 12:
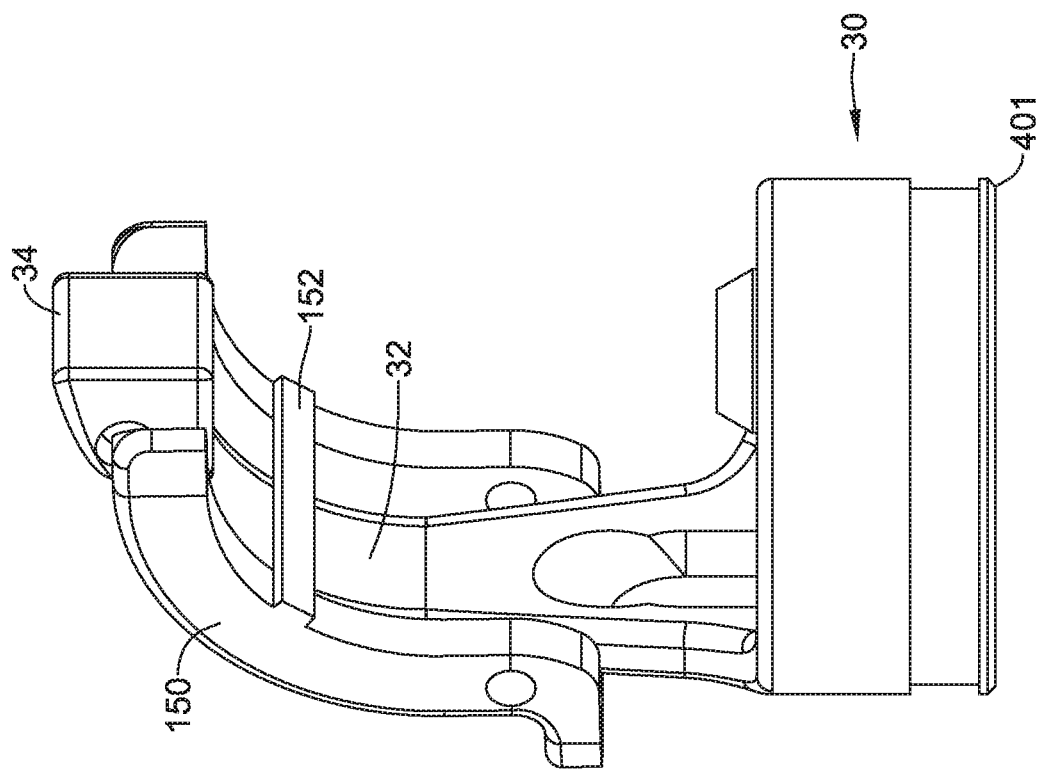
FIGS. 11 and 12 are views of a tissue release mechanism that may be used in combination with the distal assemblies of FIGS. 1 and 8 in accordance with an example of the disclosure.
Figure 11:
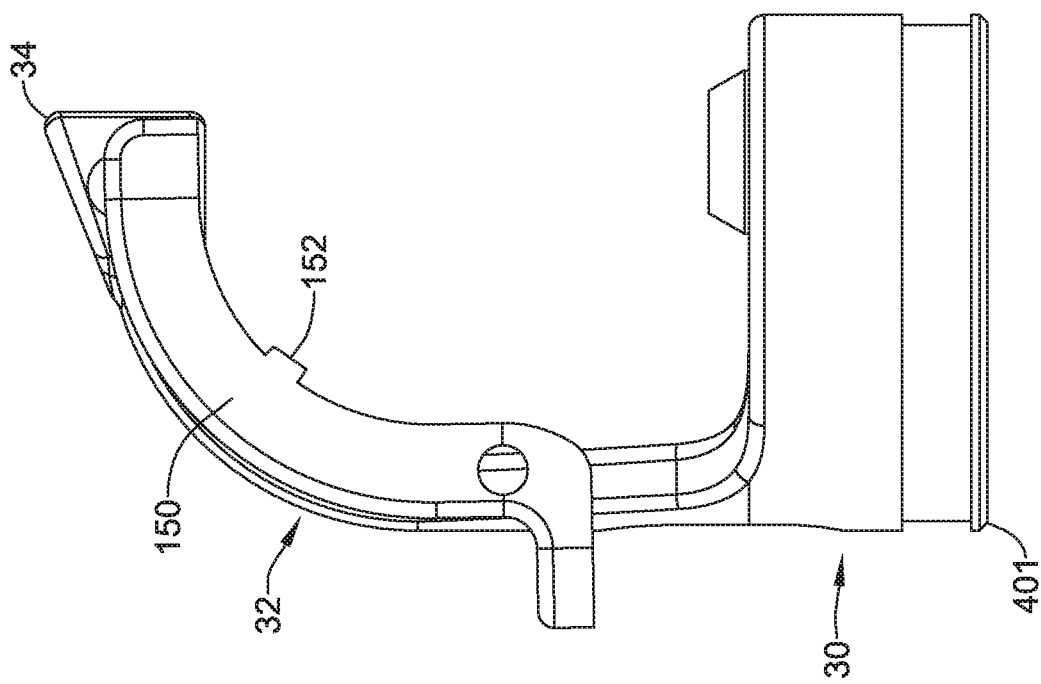

FIG. 11 and FIG. 12 are views of a tissue release mechanism 150 that may fit over the arm 32. In some embodiments, the tissue release mechanism 150 may assist in a procedure by helping to remove tissue that may otherwise become stuck on the needle 16. In some instances, the tissue release mechanism 150 may be spring-loaded to engage the needle 16, or may be separately and independently actuated. In some instances, the tissue release mechanism 150 includes a cross-bar 152 that provides an additional surface that can push tissue off of the needle 16.

In preparing the suture device 10 for use, the distal assembly 14 may be secured to a delivery device such as an endoscope. In some embodiments, an attachment enabler, such as a flexible silicone tube, may be unrolled along the delivery device in order to hold the distal assembly 14 in place and to prevent rotation of the distal assembly 14 relative to the delivery device. In some embodiments, if desired, the side-saddled lumen attachment element 120 (or 120a) may be secured to the distal assembly 14. The suture may be passed through the needle 16, and fed back towards the user interface. The device 10 may be extended through the body to the defect site.

Figure 13:
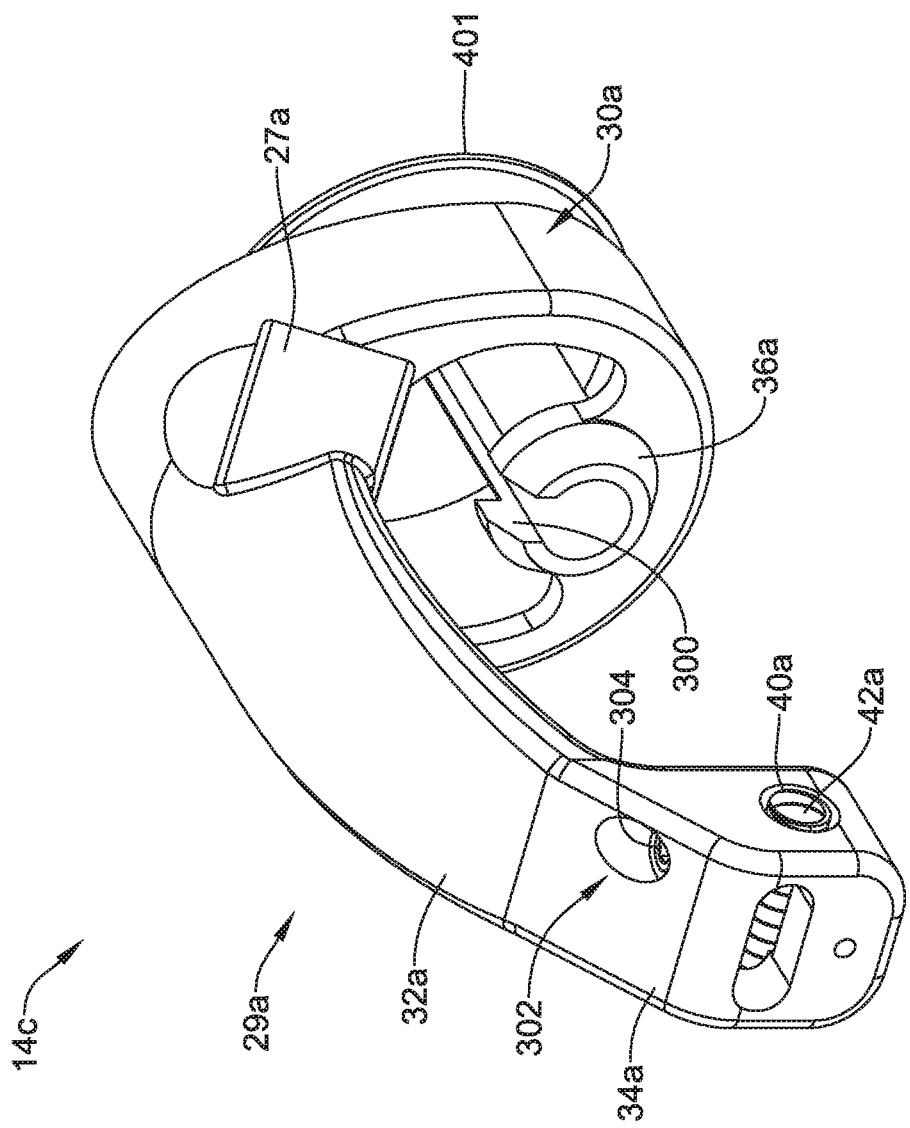
FIG. 13 is a perspective view of a distal assembly usable in the suture device of FIG. 1 in accordance with an example of the disclosure.

FIG. 13 is a perspective view of a distal assembly 14c that may, for example, be usable in the suture device 10 shown in FIG. 1. The distal assembly 14c is similar to the distal assembly 14 shown in previous Figures, but includes several modifications that may be useful, particularly in bariatric revision procedures. A bariatric procedure commonly refers to a procedure in which the effective useful volume of a patient's stomach may be surgically reduced in order to effect long-term weight loss for the patient and may be performed laparoscopically. A bariatric revision procedure is a procedure, performed endoscopically, in which changes may be made to what was originally done to the patient's stomach. In some embodiments, the distal assembly 14c may also be used in other suturing procedures, such as but not limited to full tissue thickness repairs and/or partial tissue thickness repairs.

The distal assembly 14c may include a body 29a having a proximal connector 30a that may be configured to be coupled to the distal end of an endoscope or other delivery system, for example. In some embodiments, as illustrated, the proximal connector 30a may include a fixation feature such as a fixation flange 401. The body 29a includes an arm 32a that extends to an endcap 34a. In some embodiments, the body 29a, including the arm 32a, may be similar to the body 29 and arm 32 referenced previously with respect to the distal assembly 14, the distal assembly 14a and the distal assembly 14b. In some instances, however, the body 29a and the arm 32a may be adapted to accommodate thicker tissue, which may for example mean a change in the overall shape of the body 29a and/or the arm 32a relative to the body 29 and/or the arm 32. In some embodiments, the body 29a and/or the arm 32a may simply be larger in order to accommodate thicker tissue. The distal assembly 14c may be considered as including a guide member 36a that may be secured to or integrally formed with the body 29a, and may be configured to permit a suture translation assembly (such as the suture translation assembly 12, a suture translation assembly 12a, shown in FIG. 14 through FIG. 18, or a suture translation assembly 12b, shown in FIG. 19 through FIG. 22) to extend through the guide member 36a and to translate relative to the guide member 36a.

In some embodiments, as illustrated, the guide member 36a includes a channel 300. In some embodiments, the channel 300 permits a suture to pass between the suture translation assembly 12, 12a, 12b and a working channel of the endoscope or other delivery device to which the distal assembly 14c is attached. The channel 300 may, for example, be designed to include a lead in that would help to align the suture with the channel 300 when passing the suture translation assembly 12, 12a, 12b through the working channel of the endoscope or other delivery device. In some embodiments, there may be a desire to load the suture before passing the suture translation assembly 12, 12a, 12b through the working channel of the endoscope or other delivery device.

In some instances, the distal assembly 14c includes a guide structure 27a that is attached to or integrally formed with the body 29a. In some embodiments, the guide structure 27a may instead be pivotably attached to the body 29a. The guide structure 27a may be configured to accommodate a polymeric tubular member attached thereof, in order to guide tools through the endoscope and into position relative to the working site. In some instances, the guide structure 27a may be configured to accommodate a metallic tubular member attached thereto. In some embodiments, for example, the guide structure 27a and accompanying tubular member (not illustrated) may accommodate a graspers or similar tool that allows a user to grasp tissue and pull it into position so that the needle 16 may be passed through the tissue. In some embodiments, the relative position, or offset of the guide structure 27a, relative to the relative position or offset illustrated with respect to the distal assembly 14, the distal assembly 14a or the distal assembly 14b, may be greater in order to provide more room for tools and/or to accommodate larger and/or thicker portions of tissue.

The end cap 34a includes one or more securement openings 40a that may be, as can be seen, be arranged orthogonally to a proximal needle opening (not illustrated), such as the proximal needle opening 37 illustrated for example in FIG. 3. One or more securements 42a may correspondingly be disposed within the one or more securement openings 40a. In some embodiments, the one or more securements 42a may be a coil spring that is disposed within the one or more securement openings 40a. The securement 42a may releasably engage a detent on the needle 16, as discussed with respect to the distal assembly 14.

In some embodiments, the securement opening 40a may have a diameter that is greater than an overall diameter of the securement 42a and the securement opening 40a may taper to a diameter on an opposing side (not seen) that is about the same as the diameter of the securement 42a. In some embodiments, the securement 42a may be welded, soldered, adhesively secured or otherwise attached at the left side of the securement opening 40a, and may be free to move somewhat at the right side of the securement opening 40a. In some instances, the distal assembly 14c may include an opening 302 that is orthogonal to the securement opening 40a. The opening 302 may be threaded in order to threadedly engage a set screw 304. In some embodiments, as illustrated, the opening 302 may be offset closer to the right side of the securement opening 40a, away from the secured end of the securement 42a, such that the set screw 304 may be considered as supporting the free end of the securement 42a. Rotating the set screw 304 in a first direction, such as clockwise, may cause the set screw 304 to translate towards the securement 42a, thereby increasing an interference between the securement 42a and the needle 16 and increasing a retentive force that can be applied to the needle 16. Conversely, rotating the set screw in a second direction, such as counter-clockwise, may cause the set screw 304 to translate away from the securement 42a, thereby decreasing the retentive force that can be applied to the needle 16. This may help to adjust for manufacturing tolerances, for example.

Figure 14:
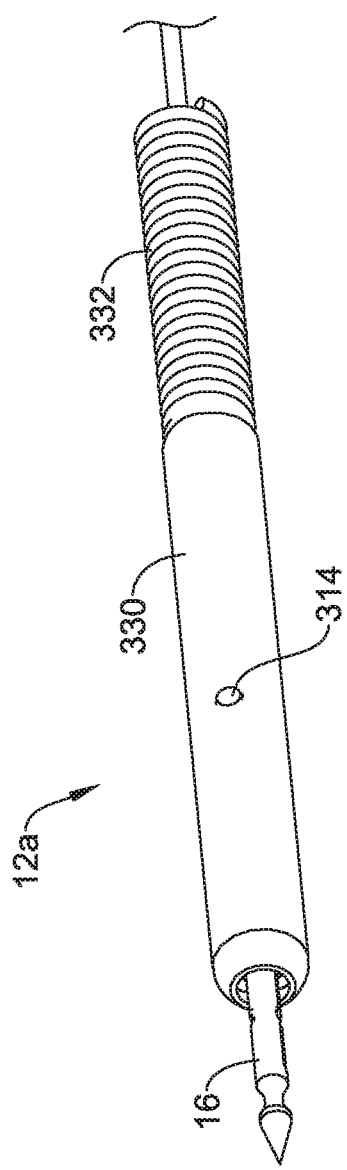
FIG. 14 is a perspective view of a suture translation assembly usable in the suture device of FIG. 1 in accordance with an example of the disclosure.
Figure 15:
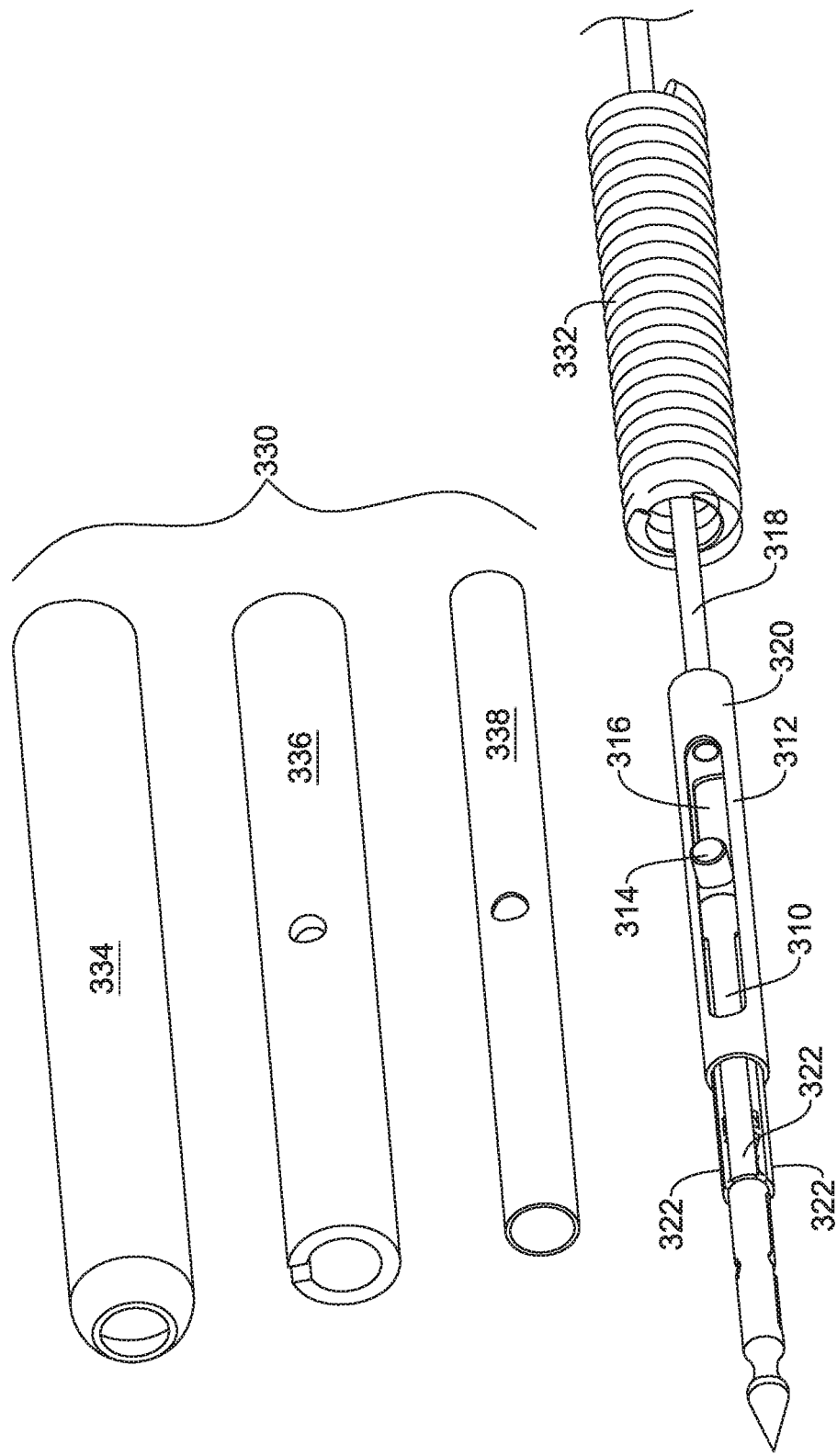
FIG. 15 is a partially exploded perspective view of the suture translation assembly of FIG. 14 in accordance with an example of the disclosure.

As noted, the distal assembly 14c may be used in combination with the suture translation assembly 12 discussed previously with respect to FIG. 5, for example. The distal assembly 14c may also be used with a suture translation assembly 12a, shown in FIG. 14 through FIG. 18, as well as with a suture translation assembly 12b, shown in FIG. 19 through FIG. 22. FIG. 14 is a perspective view of the suture translation assembly 12a, shown holding the needle 16, while FIG. 15 is a partially exploded view of the suture translation assembly 12a. As better seen in FIG. 15, the suture translation assembly 12a includes an inner member 310 that hold the needle 16. A locking member 312 is slidingly disposed over the inner member 310. As can be seen, the inner member 310 includes a pin 314 that extends radially outwardly from the inner member 310 and extends through a corresponding slot 316 that is formed in the locking member 312. The pin 314 serves to prevent relative rotation between the inner member 310 and the locking member 312. The pin 314 also serves to limit translation of the locking member 312 relative to the inner member 310.

A control member 318 is secured relative to a proximal end 320 of the locking member 312, and extends distally to a handle such as a translating handle. As a result, the locking member 312 may be translated distally and/or proximally relative to the inner member 310. As seen in FIG. 14, the suture translation assembly 12a includes an outer sleeve 330 that may be pinned via the pin 314 to the inner member 310. The outer sleeve 330 may be coupled with a coil 332, for example. In some embodiments, the outer sleeve 330 may be a single tubular member. In some embodiments, as shown for example in FIG. 15, the outer sleeve 330 may actually include one or more of an outer sleeve 334, a slotted sleeve 336, and an inner outer sleeve 338. The slotted sleeve 336 may be configured to permit a suture to pass therethrough. This is merely illustrative, and is not intended to be limiting in any fashion.

Figure 16:
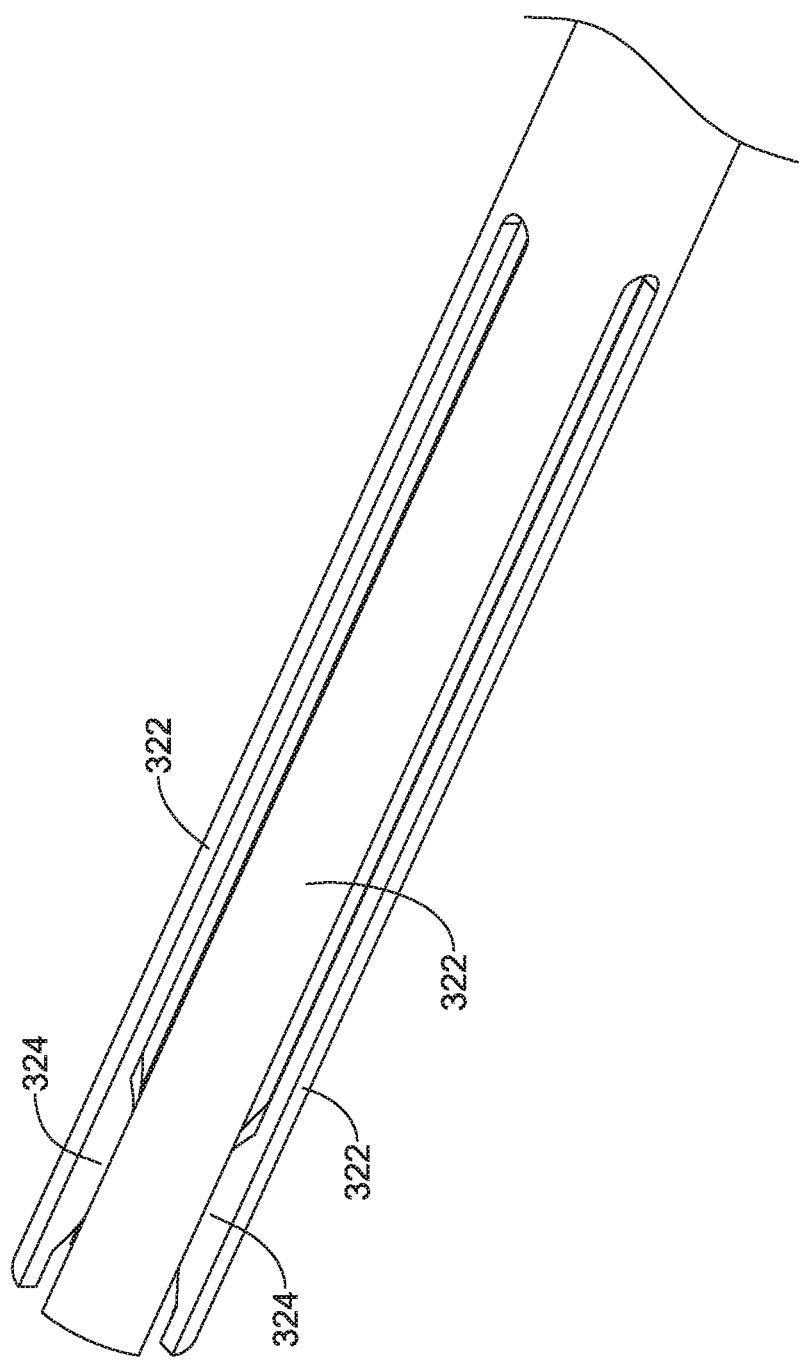
FIG. 16 is a perspective view of an inner member forming a portion of the suture translation assembly of FIG. 14 in accordance with an example of the disclosure.
Figure 17:
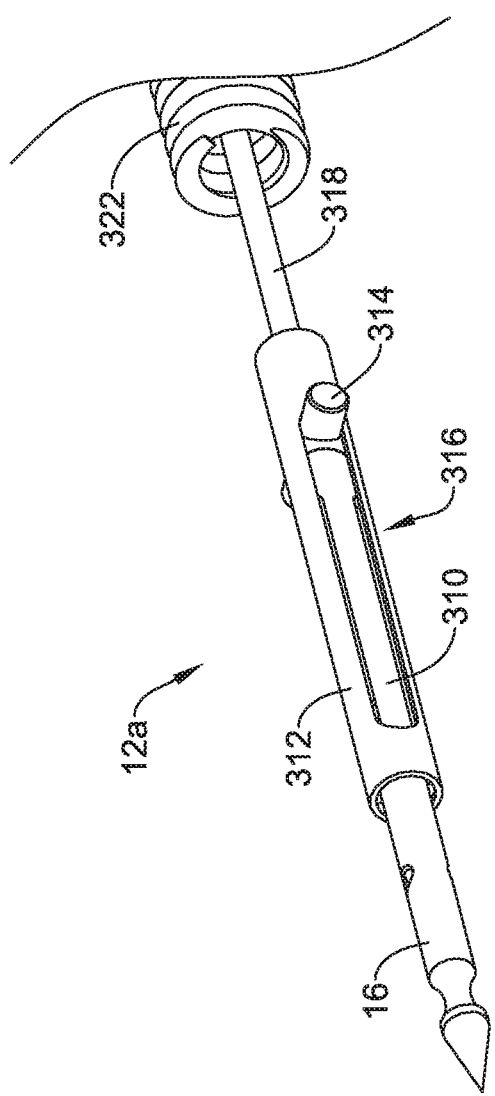
FIG. 17 is a perspective view of a portion of the suture translation assembly of FIG. 14, shown in a locked configuration in accordance with an example of the disclosure.
Figure 18:
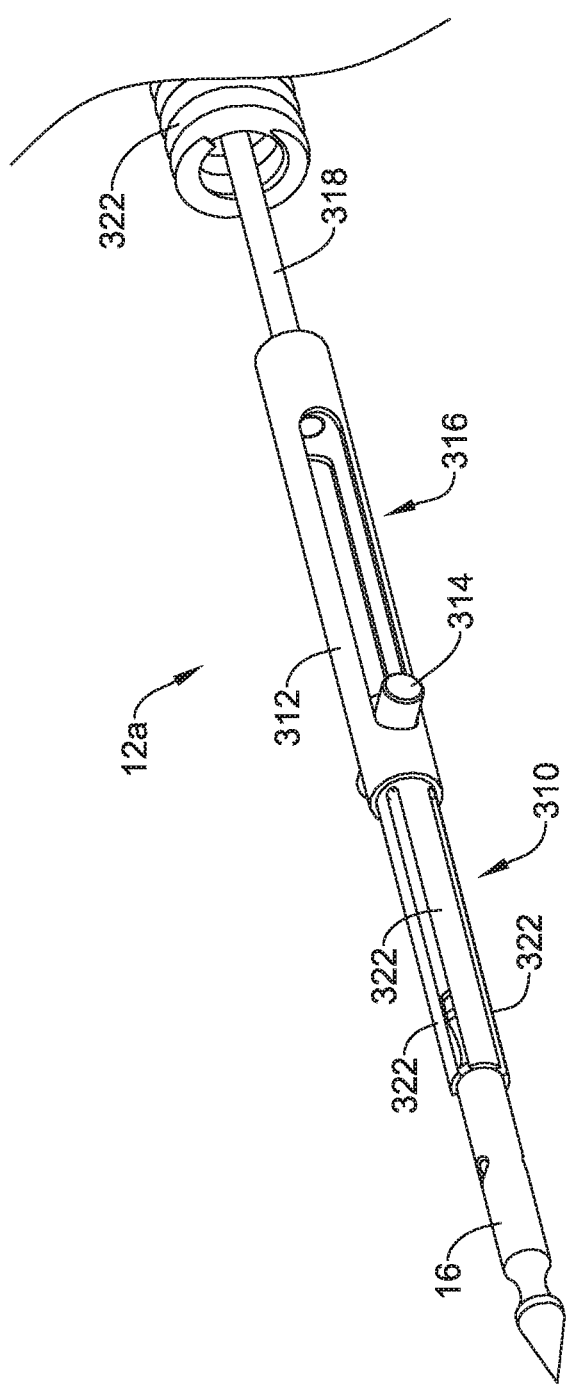
FIG. 18 is a perspective view of a portion of the suture translation assembly of FIG. 14, shown in an unlocked configuration in accordance with an example of the disclosure.

The inner member 310 includes several arms 322 that, as seen in FIG. 16, which shows the distal portion of the inner member 310, include curved tabs 324 that are configured to engage corresponding detents within the needle 16. While a total of four arms 322 are shown, it will be appreciated that the inner member 310 may include any number of arms 322. It will be appreciated that the arms 322 are relatively long in length, and as a result may be considered as being relatively flexible. With the locking member 312 extended distally into a locking configuration, as shown for example in FIG. 17, the locking member 312 prevents outward movement of the arms 322. As a result, the curved tabs 324 remain in engagement with the corresponding detents of the needle 16, and the needle 16 remains locked to the suture translation assembly 12a. With the locking member 312 retracted proximally into an unlocked configuration, as shown for example in FIG. 18, the arms 322 are free to move radially outwardly, thereby releasing the curved tabs 324 from the detents in the needle 16, and allowing the needle 16 to move distally relative to the inner member 310.

Figure 19:
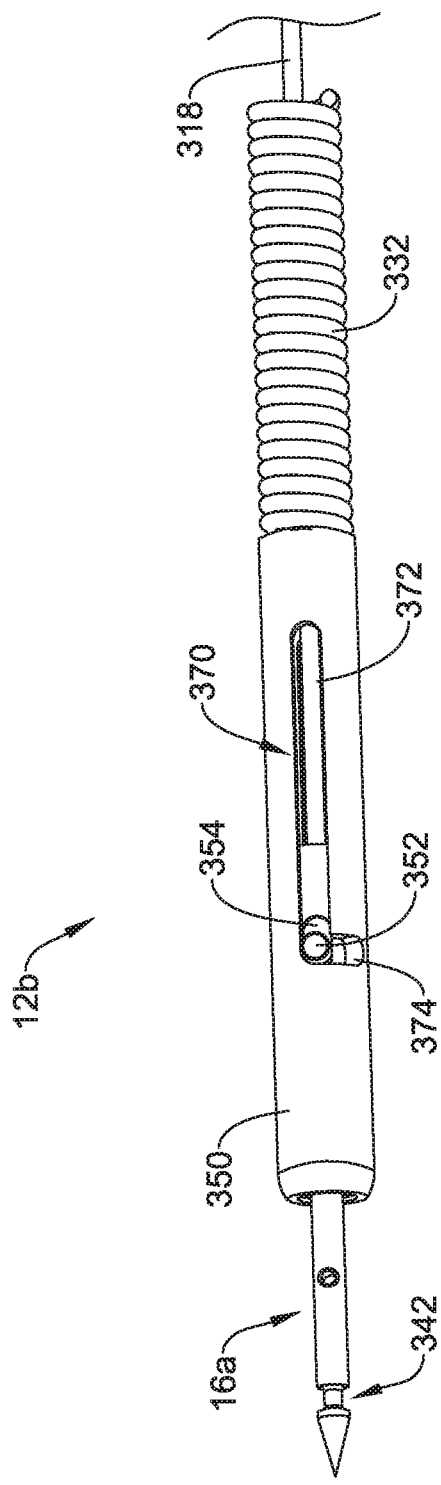
FIG. 19 is a perspective view of a suture translation assembly usable in the suture device of FIG. 1 in accordance with an example of the disclosure.
Figure 20:
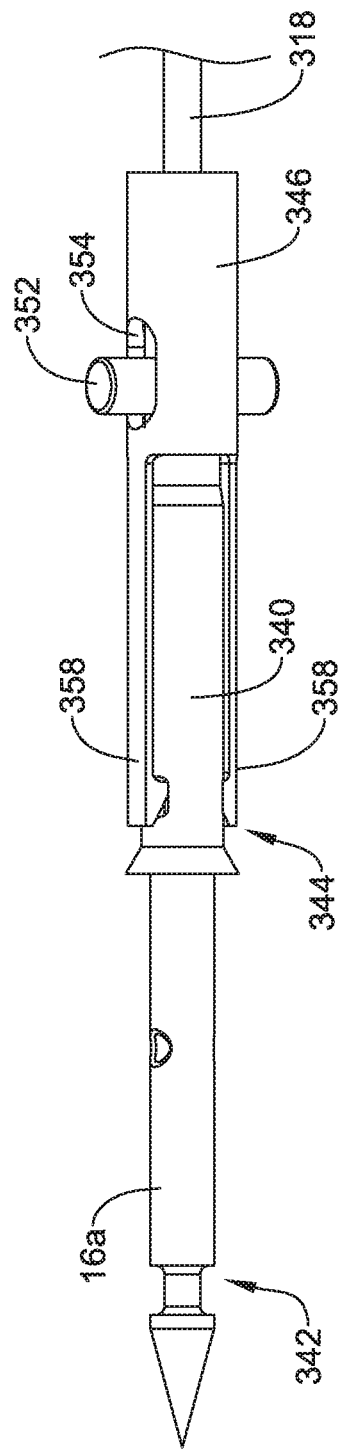
FIG. 20 is a perspective view of the suture translation assembly of FIG. 19, shown with some elements removed to show internal structure, with the suture translation assembly shown in a locked configuration in accordance with an example of the disclosure.

FIG. 19 is a perspective view of a suture translation assembly 12b that may be used in combination with any of the distal assembly 14, the distal assembly 14a, the distal assembly 14b and/or the distal assembly 14c. FIG. 20 is a perspective view of the suture translation assembly 12b with outer portions such as an outer sleeve 350 (FIG. 19) removed to reveal an inner member 340 that holds a needle 16a. In some embodiments, the outer sleeve 350 may be a single tubular member. In some instances, the outer sleeve 350 may include several elements, such as described with respect to the outer sleeve 330 (FIG. 15).

In some embodiments, as illustrated, the needle 16a has a distal detent 342 and a proximal detent 344 (visible in FIG. 21) that are shaped differently than the corresponding detents in the needle 16. The suture translation assembly 12b includes a locking member 346 that is slidingly disposable relative to the inner member 340. The pin 352 is attached to the inner member 340 and extends through a corresponding slot 354 formed in the locking member 342. The pin 352 limits translation of the locking member 342 relative to the inner member 340, and also prevents relative rotational movement of the locking member 342. The locking member 342 is secured to the control member 318, which extends distally to a handle such as a translating handle. As a result, the locking member 342 may be translated distally and/or proximally relative to the inner member 340.

In some embodiments, the outer sleeve 350 may define a slot 370 including an axially extending slot portion 372 and a shorter radially extending slot portion 374. In some embodiments, the axially extending slot portion 372 permits the pin 352 to move within the axially extending slot portion 372 in order to permit the needle 16a to be fully withdrawn into the suture translation assembly 12b for advancement through an endoscope or other delivery device. Once the suture translation assembly 12b has been advanced through the endoscope or other delivery device, the inner member 340 and the locking member 342 may be advanced distally through the outer sleeve 350 until the pin 352 aligns with the radially extending slot portion 374. By rotating a translating handle, the pin 352 may be rotated into position within the radially extending slot portion 374 so that the locking member 342 may be translated relative to the inner member 340.

Figure 21:
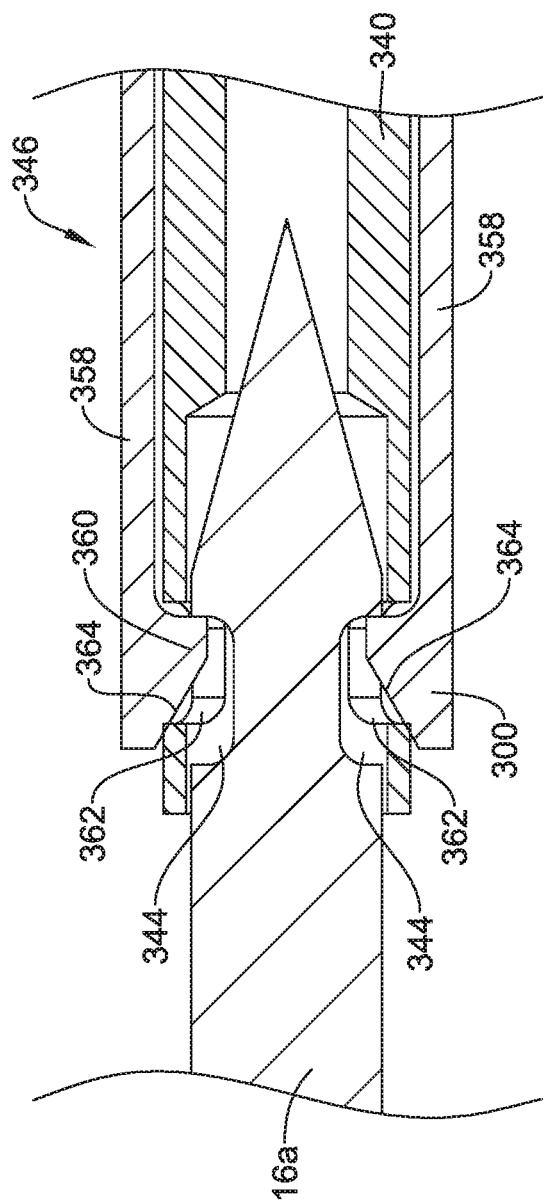
FIG. 21 is a side view of a portion of the suture translation assembly of FIG. 19, showing how a locking member engages an inner member of the suture translation assembly and a needle in the locked configuration as shown in FIG. 20 and in accordance with an example of the disclosure.

In some embodiments, as illustrated, the locking member 342 includes a pair of arms 358 that extend distally from the locking member 342. As seen for example in FIG. 21, the arms 358 include tabs 360 that, when the suture translation assembly 12b is in a locked configuration as shown in FIGS. 20 and 21, the tabs 360 extend through slots 362 formed within the inner member 340. As a result, the tabs 360 are able to extend through the slots 362 and engage the proximal detent 344 of the needle 16a. While a pair of arms 358 are illustrated, it will be appreciated that the locking member 342 may include any number of arms 358, and of course a corresponding number of slots 362.

Figure 22:
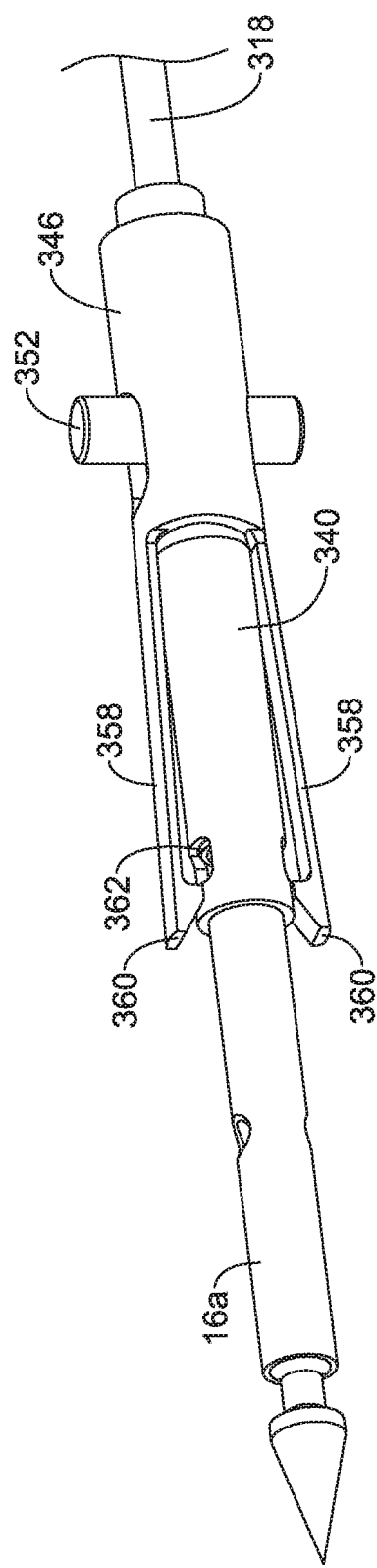
FIG. 22 is a perspective view of the suture translation assembly of FIG. 19, shown in an unlocked configuration in accordance with an example of the disclosure.

In order to move the suture translation assembly 12b into an unlocked configuration, as shown for example in FIG. 22, the locking member 342 may be moved distally relative to the inner member 340. As can be seen in FIG. 22, the tabs 360 have moved out of the slots 362 (only one slot 362 is seen), and the needle 16a is free to move relative to the suture translation assembly 12b. As the locking member 342 moves distally, angled surfaces 364 push against the slots 362 and are moved outwardly.

In some embodiments, and with respect to FIG. 13, the guide member 36a includes a channel 300 that is configured to permit a suture to pass between the suture translation assembly 12, 12a, 12b and a working channel of the endoscope or other delivery device to which the distal assembly 14c is attached. The channel 300 may, for example, be designed to include a lead in that would help to align the suture with the channel 300 when passing the suture translation assembly 12, 12a, 12b through the working channel of the endoscope or other delivery device. In some embodiments, there may be a desire to load the suture before passing the suture translation assembly 12, 12a, 12b through the working channel of the endoscope or other delivery device.

Figure 23:
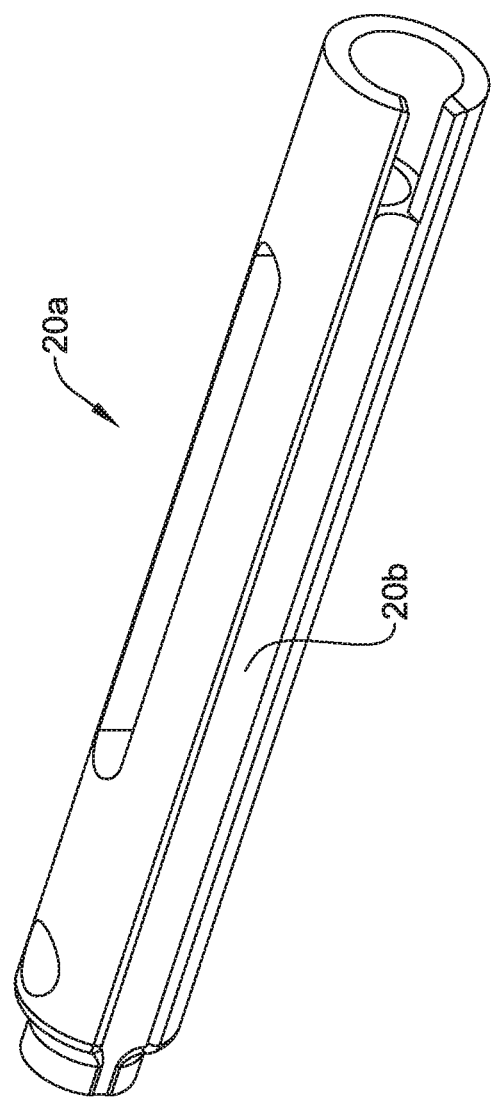
FIG. 23 is a perspective view of a sleeve usable as part of a suture translation assembly.
Figure 24:
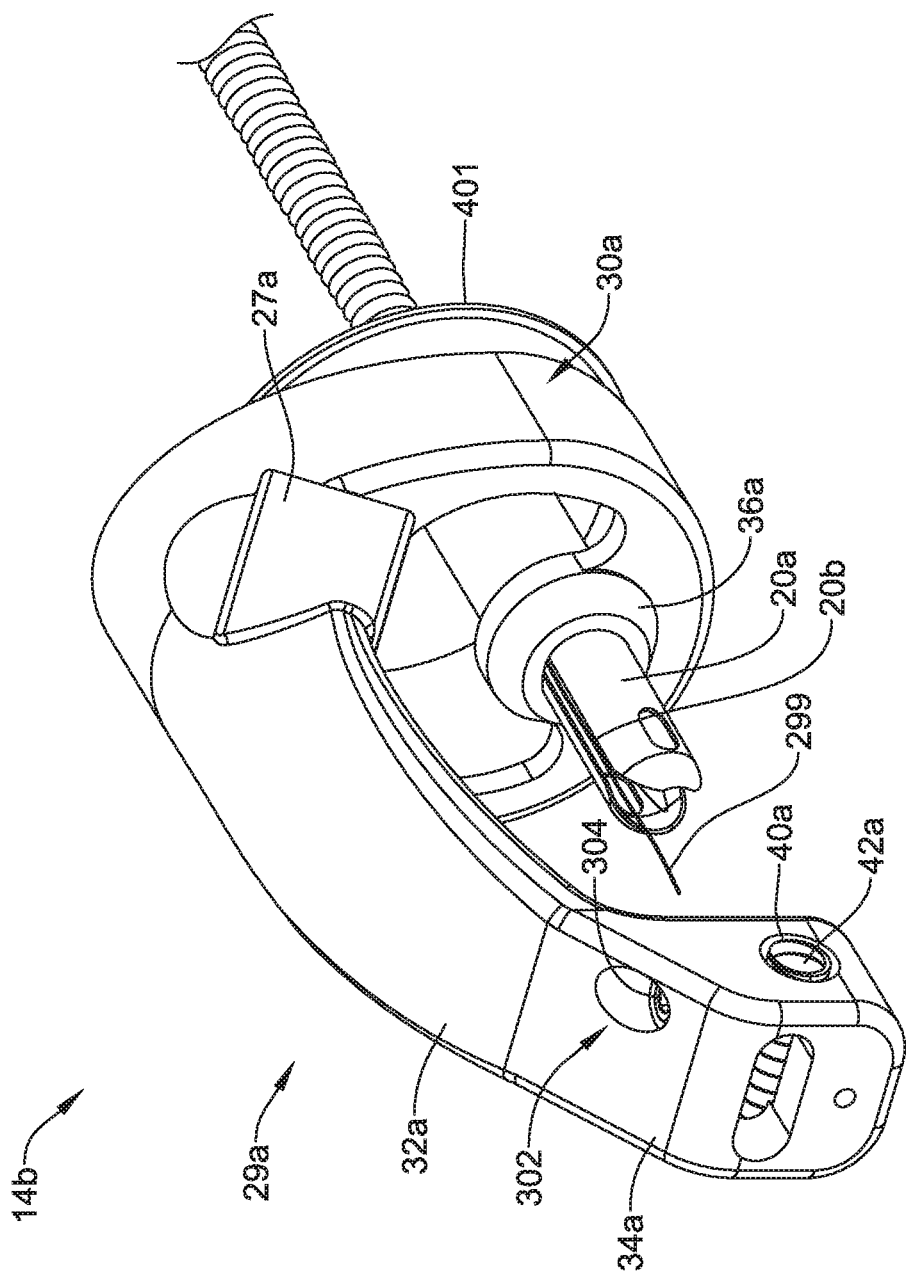
FIG. 24 is a perspective view of a distal assembly utilizing the sleeve of FIG. 23 and usable in the suture device of FIG. 1 in accordance with an example of the disclosure.

In some instances, as shown for example in FIG. 23, instead of putting a channel 300 in the guide member 36a, the suture translation assembly 12, 12a, 12b may be modified to accommodate a suture passing along the suture translation assembly 12, 12a, 12b. FIG. 23 is a perspective view of a sleeve 20a that may be used in forming a part of the suture translation assembly 12, 12a, 12b. It can be seen that the sleeve 20a includes a groove 20b that extends a length of the sleeve 20a. FIG. 24 shows the sleeve 20a extending through the guide member 36a, with a suture 299 extending through the groove 20b.

In some embodiments, there may be a desire to protect the distal end of the needle 16 when advancing the suture translation assembly 12, 12a, 12b through a delivery system such as an endoscope. In some embodiments, the needle 16 may otherwise be able to damage a working channel with the endoscope, for example. In some instances, there may be a desire to protect the needle 16 itself from becoming damaged. In some embodiments, the sleeve 20, 20a covering the needle 16 and the distal shuttle 18 (FIGS. 1-5) may be dislodged proximally during loading, resulting in possible exposure of the needle 16. In some embodiments, it may be difficult to load through a bend in the working channel of the endoscope when the sleeve 20, 20a is extended over the needle 16.

Figure 25:
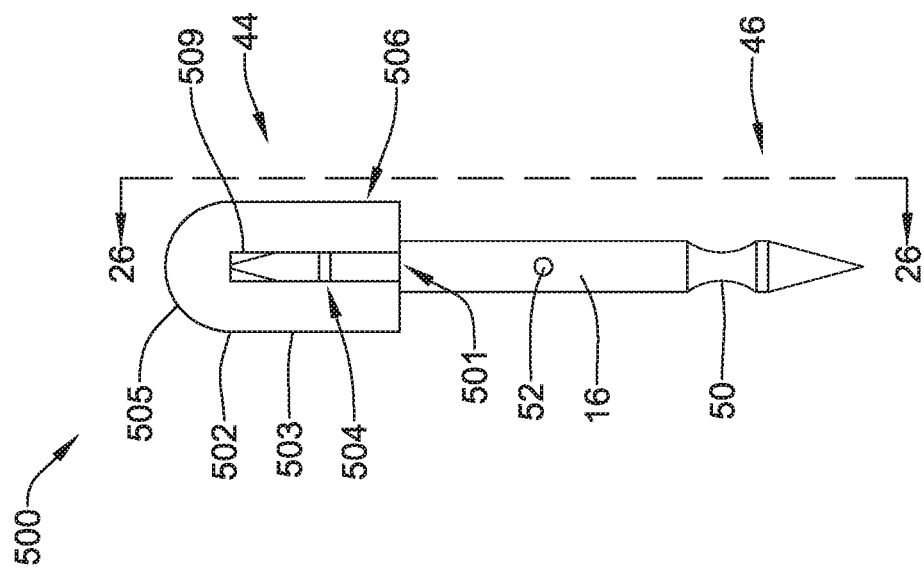
FIG. 25 is a view of a needle bearing a needle cap in accordance with an example of the disclosure.
Figure 26:
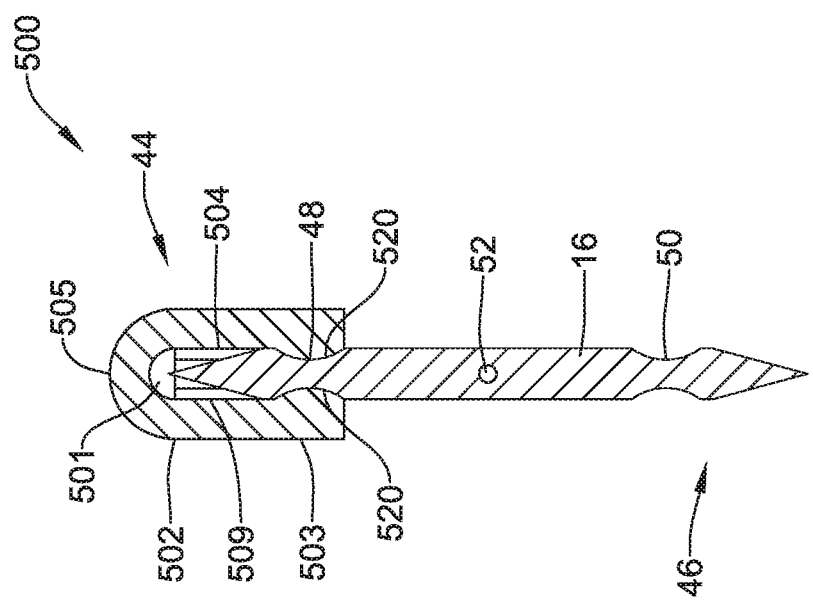
FIG. 26 is a cross-sectional view of the needle and needle cap of FIG. 25, taken along the line 26-26.

FIGS. 25 and 26 illustrate an example in which a needle cap 500 has been placed over the distal region 44 of the needle 16. FIG. 25 is a side view while FIG. 26 is a cross-sectional view taken along line 26-26 of FIG. 25. In some embodiments, the needle cap 500 may be removed outside of the patient, after the suture translation assembly 12, 12a, 12b has been loaded into the endoscope but before the endoscope has been inserted into the patient. In some embodiments, the needle cap 500 may be pushed off of the needle 16 inside the patient. When performing a procedure utilizing multiple needles and sutures, such as but not limited to endoscopic sleeve gastroplasty, it may be desirable to remove the needle cap 500 with the endoscope inside the patient so that the endoscope does not have to be removed and inserted multiple times. In some embodiments, the needle cap 500 can be pushed off of the needle 16 by moving the sleeve 20, 20a distally. In some embodiments, the needle cap 500 may be configured to split when the needle cap 500 contacts the distal endcap 14, 14a, 14b, 14c.

The needle cap 500 includes a cylindrical needle cap body 503 that defines a void 501 that is configured to fit over the needle 16. The needle cap 500 also includes an atraumatic tip 505 that is integrally molded with or otherwise attached to the cylindrical needle cap body 503. In some embodiments, the needle cap 500 includes one or more elongate slots 509 that extend axially along the cylindrical needle cap body 503 and provide sufficient flexibility to allow the needle cap 500 to flex enough to be advanced onto the needle 16. In some embodiments, there may be two slots 509, although only one is visible in FIGS. 25 and 26. The needle cap 500 includes one or more convex protuberances 520 that are configured to fit into the distal detent 48 of the needle 16. While the cylindrical needle cap body 503 is shown as having parallel sides, in some cases the needle cap 500 may have flared sides that can compress for delivery. Extending the needle 16 distally can allow the flared sides of the needle cap 500 to expand. The needle can then be withdrawn proximally to push the needle cap 500 off of the needle 16.

Figure 27:
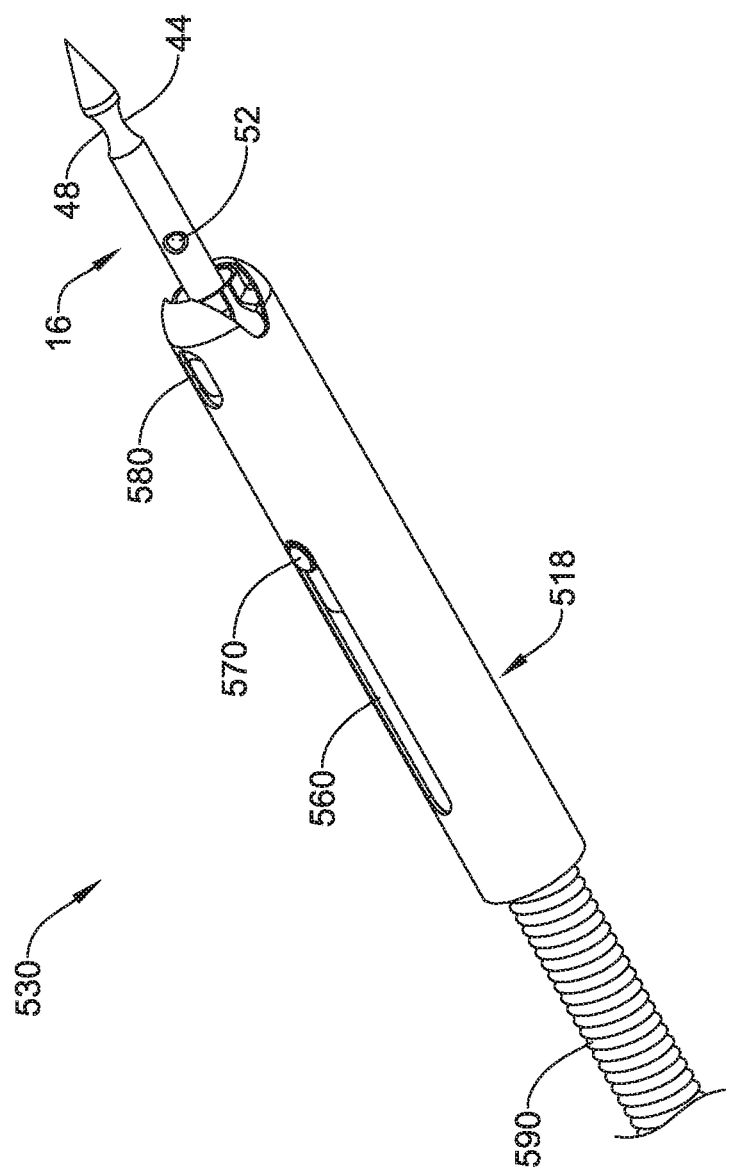
FIG. 27 is a perspective view of a suture translation assembly with a needle shown in an unlocked position in accordance with an example of the disclosure.
Figure 28:
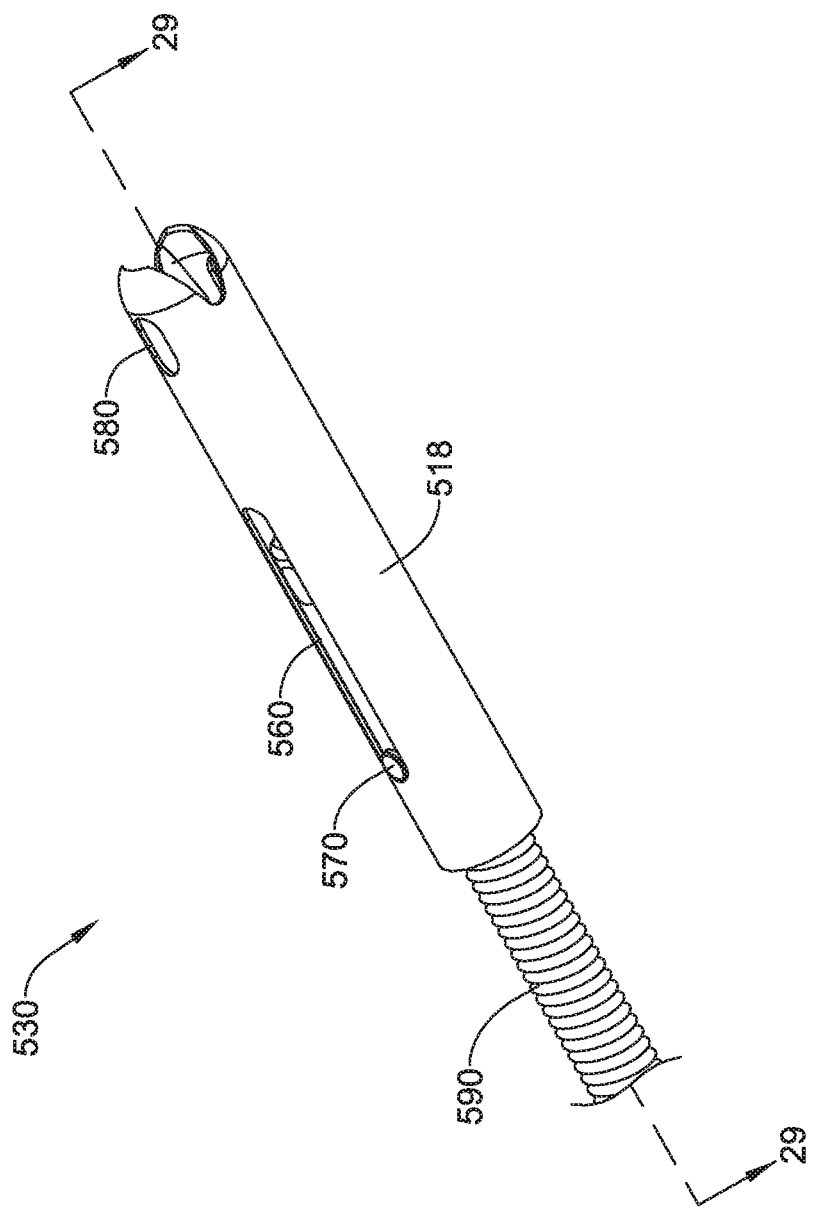
FIG. 28 is a perspective view of the suture translation assembly of FIG. 27, with the needle shown in a locked position in accordance with an example of the disclosure.

FIGS. 27 through 30 illustrate another way of protecting the needle 16, either from damaging the interior of an endoscope or from becoming damaged itself. FIGS. 27 through 30 are various views of a suture translation assembly 530 that provides a reduced overall length that facilitates loading into an endoscope. In some instances, the suture translation assembly 530 is short enough to permit easy passage through an endoscope with the sleeve in place over the needle. In some embodiments, control of the suture translation assembly 530 is reversed relative to the suture translation assemblies 12, 12a, 12b described with respect to previous Figures. FIG. 27 shows the suture translation assembly 530 in an unlocked position, in which the needle 16 is unlocked relative to the distal shuttle and can be passed to the distal endcap 14, 14a, 14b, 14c. FIG. 28 shows the suture translation assembly 530 in a locked position, in which the needle 16 is locked to the distal shuttle. As seen, the suture translation assembly 530 includes a sleeve 518 and a suture catheter 590. In some embodiments, as illustrated, the suture catheter 590 is a coil. The sleeve 518 has a pair of slots 560 (only one slot 560 is visible in the illustrated orientation) in order to accommodate movement of a distal shuttle, as will be discussed. The sleeve 518 also includes a pair of sleeve openings 580 (only one visible) that permit bearing balls 58 (not shown) to move in and out relative to a distal shuttle, thereby locking and unlocking the needle 16.

Figure 29:
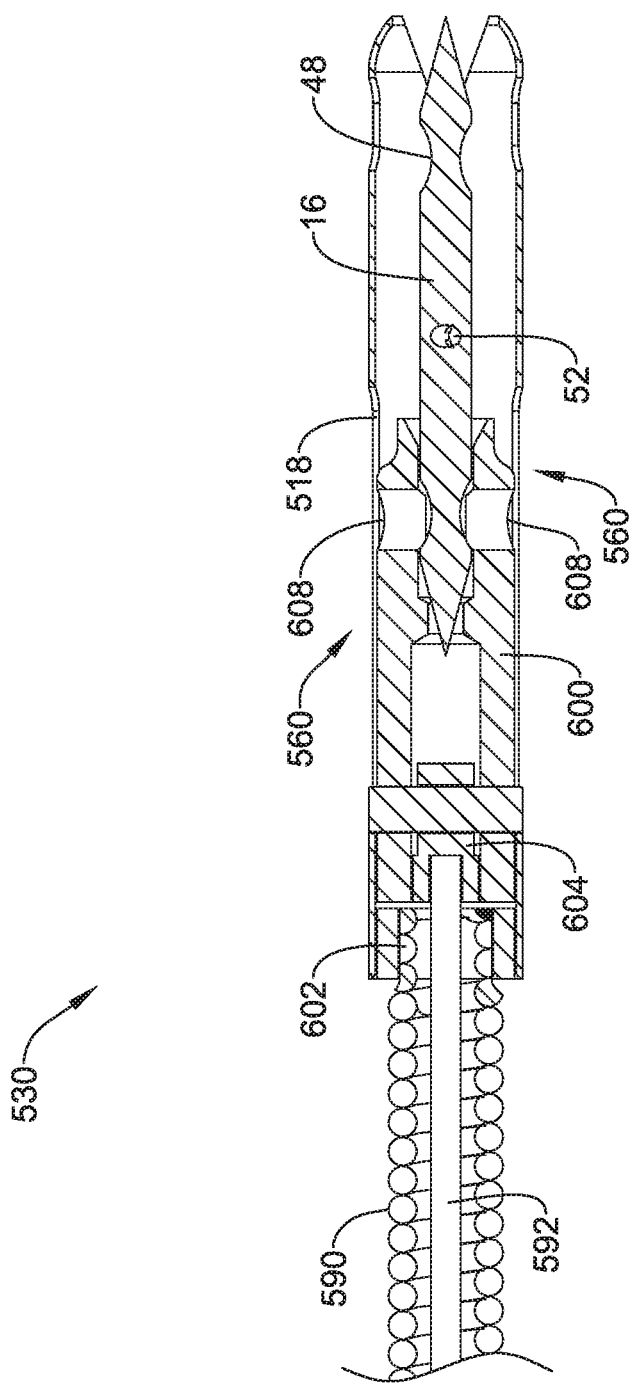
FIG. 29 is a cross-sectional view of the suture translation assembly of FIG. 28, taken along the line 29-29.
Figure 30:
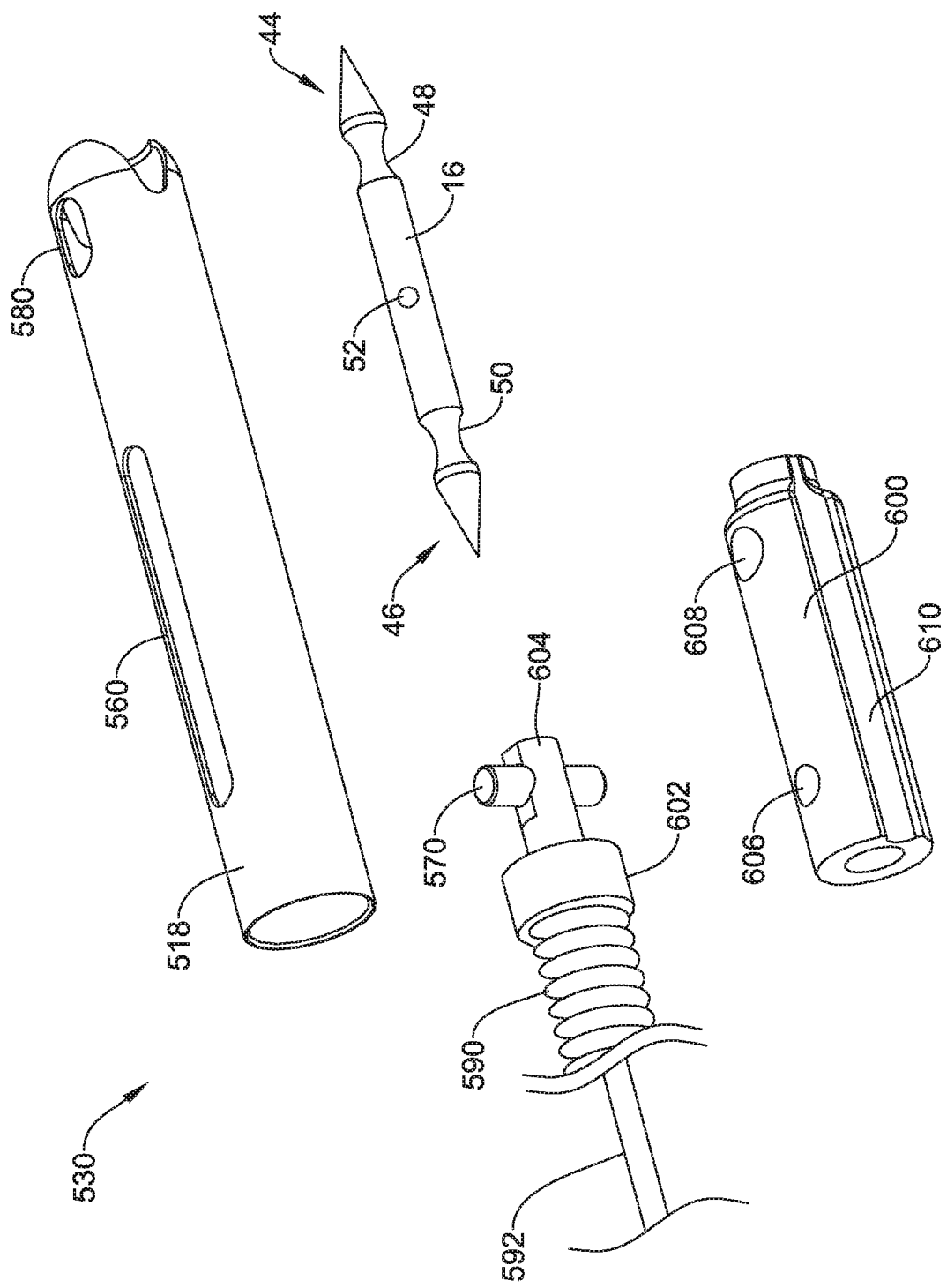
FIG. 30 is a partial exploded view of the suture translation assembly of FIG. 28.

The internal structure of the suture translation assembly 530 is better seen in FIG. 29, which is a cross-sectional view taken along the line 29-29 of FIG. 28, as well as FIG. 30, which is a partially exploded view of FIG. 28. As can be seen, a control wire 592 extends through the suture catheter 590 and terminates within a yoke 604. The sleeve 518 is coupled to the suture catheter 590 via a coupler 602. In some embodiments, the sleeve 518 may be welded to the suture catheter 590, either directly or by being welded to the coupler 602. As a result, the sleeve 518 does not move relative to the suture catheter 590.

A pin 570 extends through the yoke 602 and into apertures 606 that are formed within a distal shuttle 600, thereby operably coupling the control wire 592 to the distal shuttle 600. The pin 570 extends to and is guided by a pair of slots 560 that are formed in the sleeve 518. This prevents rotation of the distal shuttle 600 relative to the sleeve 518. In some embodiments, the distal shuttle 600 includes a groove 610 that allows a suture to extend from the needle 16 and extend axially through the sleeve 518.

The distal shuttle 600 also includes a pair of bearing ball openings 608. As discussed previously, when the bearing ball openings 608 are aligned with the sleeve openings 580, the bearing balls 58 (not shown) are free to move radially outwardly sufficiently to clear the proximal detent 50 of the needle 16, thereby unlocking the needle 16 from the distal shuttle 600. Conversely, when the bearing ball openings 608 are misaligned with the sleeve openings 580, the bearing balls 58 (not shown) are not able to clear the proximal detent 50 of the needle 16, and the needle 16 remains locked to the distal shuttle 600. Accordingly, moving the control wire 592 in a proximal direction moves the distal shuttle 600 in a proximal direction relative to the sleeve 518. This causes the sleeve openings 580 to misalign with the bearing ball openings 608 and locks the needle 16 to the sleeve 518. Conversely, moving the control wire 592 in a distal direction moves the distal shuttle 600 in a distal direction relative to the sleeve 518.

It will be appreciated that a variety of different materials may be used in forming the devices described herein. In some embodiments, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b- styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A suture device for use in combination with an endoscope having a working channel and a distal end, the suture device comprising:
    a needle configured to carry a suture, the needle including a distal end and a distal detent near the distal end;
    a protective needle cap configured to releasably fit over the distal end of the needle, the needle cap including an atraumatic distal tip and a cylindrical needle cap body defining a void that is configured to fit over the needle, wherein the protective needle cap is formed of a biosorbable polymer;
    a distal shuttle configured to releasably secure the needle; and
    a sleeve disposable over the distal shuttle, the sleeve movable between a locked position in which the needle is secured to the distal shuttle and an unlocked position in which the needle is releasable from the distal shuttle;
    wherein the protective needle cap is configured to be pushed off the needle inside of the patient by moving the sleeve distally;
    a distal endcap configured to be securable to a distal end of the endoscope, the distal endcap configured to releasably engage and disengage the needle, the endcap configured to engage the needle when the needle is advanced distally into the endcap, and to release the needle when the needle is locked to the distal shuttle and the distal shuttle is withdrawn proximally.

2. The suture device of claim 1, wherein the protective needle cap further comprises one or more elongate slots extending axially within the cylindrical needle cap body.

3. The suture device of claim 2, wherein the protective needle cap further comprises one or more convex protuberances extending into the void, the one or more convex protuberances configured to fit into the distal detent of the needle.

4. A suture device for use in combination with a delivery system including a lumen extending through the delivery system, the suture device comprising:
    a suture translation assembly configured to be axially translatable within the lumen of the delivery system, the delivery system including a distal end, the suture translation assembly including:
        a needle usable to carry a suture;
        a distal shuttle configured to releasably secure the needle;
        a sleeve disposable over the distal shuttle, the distal shuttle movable relative to the sleeve between a locked position in which the needle is locked to the distal shuttle and an unlocked position in which the needle is releasable from the distal shuttle;
    a suture catheter operably coupled to the sleeve via a coupler;
    a control wire operably coupled to the distal shuttle and terminating in a yoke joining the control wire to the distal shuttle; and
    a distal endcap configured to be securable to the distal end of the delivery system, the distal endcap configured to releasably engage and disengage the needle, the endcap configured to engage the needle when the needle is advanced distally into the endcap, and to release the needle when the needle is locked to the distal shuttle and the distal shuttle is withdrawn proximally.

5. The suture device of claim 4, wherein moving the control wire proximally causes the distal shuttle to move proximally relative to the sleeve, thereby locking the needle to the distal shuttle.

6. The suture device of claim 4, wherein moving the control wire distally causes the distal shuttle to move distally relative to the sleeve, thereby releasing the needle from the distal shuttle.

7. The suture device of claim 4, wherein the needle comprises a distal region and a proximal region, the distal region including a distal detent for releasably engaging the distal endcap, the proximal region including a proximal detent for releasably engaging the distal shuttle.

8. The suture device of claim 7, wherein the distal shuttle includes:
    one or more bearing ball openings arranged to align with the proximal detent when the needle is secured to the distal shuttle; and
    one or more bearing balls disposed within the one or more bearing ball openings and disposable within the proximal detent when the needle is secured to the distal shuttle.

9. The suture device of claim 8, wherein the sleeve comprises one or more sleeve openings smaller in diameter than the one or more bearing balls;
    wherein when in the locked position, the one or more sleeve openings are misaligned with the one or more bearing ball openings such that the one or more bearing balls engage the proximal detent of the needle; and
    wherein when in the unlocked position, the one or more sleeve openings are aligned with the one or more bearing ball openings such that the one or more bearing balls can move radially outward a distance sufficient to permit the one or more bearing balls to clear the proximal detent of the needle.

10. The suture device of claim 4, wherein the yoke couples the control wire to the distal shuttle via a pin that extends through the yoke and translates along a pair of slots formed in the sleeve.

11. The suture device of claim 4, wherein the suture catheter includes a coil, and the coil is operably coupled to the sleeve.

12. The suture device of claim 11, wherein the sleeve is welded to the coil.

13. The suture device of claim 4, wherein the control wire extends through the suture catheter.

14. The suture device of claim 4, further comprising a user interface that is operably coupled to the suture catheter and the control wire, the user interface configured to permit a user to move the control wire, and thus the distal shuttle, relative to the suture catheter.

15. A suture device for use in combination with an endoscope including a lumen extending through the endoscope, the suture device comprising:
    a needle usable to carry a suture;
    a distal shuttle configured to releasably secure the needle;
    a sleeve disposable over the distal shuttle, the distal shuttle movable relative to the sleeve between a locked position in which the needle is locked to the distal shuttle and an unlocked position in which the needle is releasable from the distal shuttle;

a shaft operably coupled to the sleeve;

a control wire extending through the shaft and operably coupled to the distal shuttle via a yoke;

a distal endcap configured to be securable to the distal end of the endoscope, the distal endcap configured to releasably engage and disengage the needle, the endcap configured to engage the needle when the needle is advanced distally into the endcap, and to release the needle when the needle is locked to the distal shuttle and the distal shuttle is withdrawn proximally; and a user interface configured to allow a user to manipulate the control wire relative to the shaft in order to move the distal shuttle between its locked position and its unlocked position.

\* \* \* \* \*